(12) United States Patent
Kshirsagar et al.

(10) Patent No.: US 12,201,467 B2
(45) Date of Patent: Jan. 21, 2025

(54) MOTION, COMPRESSION, AND POSITIONING CORRECTIONS IN MEDICAL IMAGING

(71) Applicant: Hologic, Inc., Marlborough, MA (US)

(72) Inventors: Ashwini Kshirsagar, Santa Clara, CA (US); Nikolaos Gkanatsios, Danbury, CT (US); John Laviola, Orange, CT (US)

(73) Assignee: Hologic, Inc., Marlborough, MA (US)

( * ) Notice: Subject to any disclaimer, the term of this patent is extended or adjusted under 35 U.S.C. 154(b) by 802 days.

(21) Appl. No.: 16/779,178

(22) Filed: Jan. 31, 2020

(65) Prior Publication Data

US 2020/0178926 A1    Jun. 11, 2020

Related U.S. Application Data

(63) Continuation-in-part of application No. PCT/IB2018/056208, filed on Aug. 16, 2018.
(Continued)

(51) Int. Cl.
*A61B 6/00* (2024.01)
*A61B 6/03* (2006.01)
(Continued)

(52) U.S. Cl.
CPC .............. *A61B 6/527* (2013.01); *A61B 6/035* (2013.01); *A61B 6/0414* (2013.01); *A61B 6/461* (2013.01);
(Continued)

(58) Field of Classification Search
CPC ....... A61B 6/572; A61B 6/035; A61B 6/0414; A61B 6/461; A61B 6/463; A61B 6/465;
(Continued)

(56) References Cited

U.S. PATENT DOCUMENTS

| 3,578,971 A | 5/1971 | Lasky |
|---|---|---|
| 3,971,950 A | 7/1976 | Evans et al. |

(Continued)

FOREIGN PATENT DOCUMENTS

| AU | 2008201638 | 5/2008 |
|---|---|---|
| CN | 1586399 | 3/2005 |

(Continued)

OTHER PUBLICATIONS

PCT Invitation to Pay additional Fees, in Application PCT/US2021/013716, mailed May 6, 2021, 17 pages.
(Continued)

*Primary Examiner* — Joel Lamprecht
*Assistant Examiner* — Adam D. Kolkin
(74) *Attorney, Agent, or Firm* — Merchant & Gould P.C.

(57) ABSTRACT

Methods and systems for imaging. For example, a system may include a breast compression paddle, an imaging detector, at least one sensor incorporated into at least one of the breast compression paddle or the imaging detector. The system performs operations including generating, at a first time point, first spatial data of the breast based on data captured by the at least one sensor; generating, at a second time point, second spatial data of the breast based on data captured by the at least one sensor; based on the first spatial data and the second spatial data, determining an amount of motion of the breast that occurred; and based on the determined amount of motion performing at least one of: generating a motion map for the breast; discarding one or more acquired projections for use in generating a tomosynthesis reconstruction; or correcting a medical image acquired the second time point.

19 Claims, 23 Drawing Sheets

Related U.S. Application Data

(60) Provisional application No. 62/546,167, filed on Aug. 16, 2017.

(51) Int. Cl.
*A61B 6/04* (2006.01)
*A61B 6/46* (2024.01)
*A61B 6/50* (2024.01)
*A61B 6/02* (2006.01)
*A61B 8/00* (2006.01)
*A61B 8/08* (2006.01)
*A61B 8/13* (2006.01)

(52) U.S. Cl.
CPC .............. *A61B 6/463* (2013.01); *A61B 6/465* (2013.01); *A61B 6/502* (2013.01); *A61B 6/5258* (2013.01); *A61B 6/54* (2013.01); *A61B 6/025* (2013.01); *A61B 6/566* (2013.01); *A61B 8/0825* (2013.01); *A61B 8/13* (2013.01); *A61B 8/4254* (2013.01)

(58) Field of Classification Search
CPC ......... A61B 6/502; A61B 6/5258; A61B 6/54; A61B 6/025; A61B 6/566; A61B 8/0825; A61B 8/13; A61B 8/4254
See application file for complete search history.

(56) References Cited

U.S. PATENT DOCUMENTS

| | | |
|---|---|---|
| 4,496,557 A | 1/1985 | Malen |
| 4,567,899 A | 2/1986 | Kamens et al. |
| 4,943,986 A | 7/1990 | Barbarisi |
| 4,962,515 A | 10/1990 | Kopans |
| 5,040,198 A | 8/1991 | Hixson, Sr. |
| 5,051,904 A | 9/1991 | Griffith |
| 5,107,255 A | 4/1992 | Shiraishi |
| 5,199,056 A | 3/1993 | Darrah |
| 5,257,121 A | 10/1993 | Steinberg |
| 5,359,637 A | 10/1994 | Webber |
| 5,398,272 A | 3/1995 | Bouscary et al. |
| 5,474,072 A | 12/1995 | Shmulewitz |
| 5,506,877 A | 4/1996 | Niklason |
| 5,553,111 A | 9/1996 | Moore et al. |
| D376,012 S | 11/1996 | Hixson, Sr. |
| 5,706,327 A | 1/1998 | Adamkowski |
| 6,049,583 A | 4/2000 | Galkin |
| 6,122,542 A | 9/2000 | Lee |
| 6,289,235 B1 | 9/2001 | Webber |
| 6,577,702 B1 | 6/2003 | Lebovic et al. |
| 6,587,578 B2 | 7/2003 | Godik et al. |
| 6,647,092 B2 | 11/2003 | Eberhard |
| 6,682,484 B1 | 1/2004 | Entrekin et al. |
| 6,765,984 B2 | 7/2004 | Higgins et al. |
| 6,850,590 B2 | 8/2005 | Galkin |
| 6,968,033 B2 | 11/2005 | Lebovic et al. |
| 6,974,255 B1 | 12/2005 | Hixson, Sr. |
| 6,975,701 B2 | 12/2005 | Galkin |
| 7,123,684 B2 | 10/2006 | Jing et al. |
| 7,203,348 B1 | 4/2007 | Karrsemeijer |
| 7,245,694 B2 | 7/2007 | Jing et al. |
| 7,319,735 B2 | 1/2008 | DeFreitas |
| 7,430,272 B2 | 9/2008 | Jing et al. |
| 7,489,761 B2 | 2/2009 | DeFreitas et al. |
| 7,505,555 B2 | 3/2009 | Hermann et al. |
| 7,512,211 B2 | 3/2009 | Galkin |
| 7,583,786 B2 | 9/2009 | Jing et al. |
| 7,634,049 B2 | 12/2009 | Galkin |
| 7,639,780 B2 | 12/2009 | Minyard |
| 7,656,993 B2 | 2/2010 | Hoernig |
| 7,702,142 B2 | 4/2010 | Ren et al. |
| 7,742,558 B2 | 6/2010 | Mertelmeier et al. |
| 7,792,244 B2 | 9/2010 | DeFreitas et al. |
| 7,822,457 B2 | 10/2010 | Lokhandwalla et al. |
| 7,831,296 B2 | 11/2010 | Defreitas |
| 7,869,563 B2 | 1/2011 | Defreitas et al. |
| 8,155,421 B2 | 4/2012 | Ren et al. |
| 8,175,219 B2 | 5/2012 | DeFreitas et al. |
| 8,787,522 B2 | 7/2014 | Smith et al. |
| 9,050,009 B2 | 6/2015 | Den Heeten |
| 9,226,718 B1 | 1/2016 | Baxley |
| 9,332,947 B2 | 5/2016 | DeFreitas et al. |
| 9,498,180 B2 | 11/2016 | Ren et al. |
| 9,649,075 B2 | 5/2017 | DeFreitas et al. |
| 9,743,997 B2 | 8/2017 | Grimbergen |
| 9,782,135 B2 | 10/2017 | Stango et al. |
| 9,826,950 B2 | 11/2017 | Den Heeten |
| 10,603,002 B2 | 3/2020 | Stango |
| 10,888,292 B2 | 1/2021 | Stango |
| 11,259,759 B2 | 3/2022 | Stango et al. |
| 11,633,164 B2 | 4/2023 | Stango |
| 11,950,941 B2 | 4/2024 | Stango |
| 2001/0038861 A1 | 11/2001 | Hsu |
| 2002/0032373 A1 | 3/2002 | Godik et al. |
| 2002/0061090 A1 | 5/2002 | Lindstrom |
| 2003/0007597 A1 | 1/2003 | Higgins et al. |
| 2003/0007598 A1 | 1/2003 | Wang et al. |
| 2003/0099325 A1 | 5/2003 | Galkin |
| 2003/0174807 A1 | 9/2003 | Lebovic |
| 2004/0066882 A1 | 4/2004 | Eberhard |
| 2004/0066884 A1 | 4/2004 | Claus |
| 2004/0066904 A1 | 4/2004 | Eberhard |
| 2004/0094167 A1* | 5/2004 | Brady ................. G06T 7/55 600/443 |
| 2004/0156472 A1 | 8/2004 | Galkin |
| 2004/0218727 A1 | 11/2004 | Shoenfeld |
| 2005/0008117 A1 | 1/2005 | Livingston |
| 2005/0063509 A1 | 3/2005 | DeFreitas et al. |
| 2005/0113681 A1 | 5/2005 | DeFreitas et al. |
| 2005/0113683 A1 | 5/2005 | Lokhandwalla et al. |
| 2005/0113863 A1 | 5/2005 | Ramzipoor et al. |
| 2006/0050844 A1 | 3/2006 | Galkin |
| 2006/0165215 A1 | 7/2006 | Galkin |
| 2007/0081625 A1 | 4/2007 | Sendai |
| 2007/0223652 A1 | 9/2007 | Galkin |
| 2007/0242794 A1 | 10/2007 | Stanton |
| 2007/0280412 A1 | 12/2007 | DeFreitas |
| 2008/0043904 A1 | 2/2008 | Hoernig |
| 2008/0080668 A1 | 4/2008 | Kashiwagi |
| 2008/0087830 A1* | 4/2008 | Kashiwagi ............ A61B 5/103 250/363.05 |
| 2008/0181361 A1 | 7/2008 | Eldered et al. |
| 2008/0240345 A1 | 10/2008 | Galkin |
| 2008/0242979 A1* | 10/2008 | Fisher ................. A61B 8/4416 600/427 |
| 2008/0247508 A1 | 10/2008 | Harrington |
| 2009/0003519 A1 | 1/2009 | DeFreitas et al. |
| 2009/0135997 A1 | 5/2009 | DeFreitas |
| 2009/0175408 A1 | 7/2009 | Goodsitt et al. |
| 2009/0262887 A1 | 10/2009 | Iordache |
| 2009/0268865 A1 | 10/2009 | Ren |
| 2009/0304146 A1 | 12/2009 | Ramsauer |
| 2009/0324049 A1* | 12/2009 | Kontos ................. G06T 7/40 382/173 |
| 2010/0046698 A1 | 2/2010 | Lebovic et al. |
| 2010/0049093 A1 | 2/2010 | Galkin |
| 2010/0111249 A1 | 5/2010 | Mertelmeir et al. |
| 2011/0058724 A1 | 3/2011 | Claus |
| 2011/0064190 A1 | 3/2011 | Ruimi |
| 2011/0087098 A1* | 4/2011 | Fischer ................. A61B 6/502 600/439 |
| 2011/0257919 A1 | 5/2011 | Reiner |
| 2012/0033868 A1* | 2/2012 | Ren ..................... A61B 6/502 378/21 |
| 2012/0051522 A1 | 3/2012 | Nishino |
| 2012/0114095 A1 | 5/2012 | Smith et al. |
| 2012/0277625 A1 | 11/2012 | Nakayama |
| 2013/0012837 A1 | 1/2013 | Krogure |
| 2013/0028499 A1 | 1/2013 | Tsujii |
| 2013/0051520 A1 | 2/2013 | Ramsauer |
| 2013/0129039 A1 | 5/2013 | DeFreitas et al. |
| 2013/0272493 A1 | 10/2013 | Otokuni |
| 2014/0107493 A1 | 4/2014 | Yuen |

(56) References Cited

U.S. PATENT DOCUMENTS

| | | | |
|---|---|---|---|
| 2014/0296701 A1 | 10/2014 | Hancu et al. | |
| 2014/0328458 A1* | 11/2014 | Erhard | A61B 6/0414 702/19 |
| 2014/0378816 A1 | 12/2014 | Oh | |
| 2015/0272682 A1 | 10/2015 | Sheng | |
| 2015/0282770 A1 | 10/2015 | Klanian et al. | |
| 2016/0066875 A1 | 3/2016 | Jacob et al. | |
| 2016/0081633 A1 | 3/2016 | Stango et al. | |
| 2016/0183889 A1 | 6/2016 | Matsuura | |
| 2016/0242707 A1 | 8/2016 | Defreitas et al. | |
| 2017/0055930 A1 | 3/2017 | Hagiwara | |
| 2017/0251991 A1 | 9/2017 | Wang | |
| 2017/0340303 A1 | 11/2017 | Stango | |
| 2017/0347976 A1 | 12/2017 | DeFreitas et al. | |
| 2018/0125437 A1 | 5/2018 | Stango et al. | |
| 2018/0165840 A1 | 6/2018 | Bernard | |
| 2018/0184999 A1 | 7/2018 | Davis | |
| 2020/0069274 A1 | 3/2020 | Stango | |
| 2020/0196971 A1 | 6/2020 | Laviola | |
| 2020/0359974 A1 | 11/2020 | DeFreitas | |
| 2020/0359975 A1 | 11/2020 | Banks | |
| 2020/0390405 A1 | 12/2020 | DeFreitas | |
| 2021/0015435 A1 | 1/2021 | DeFreitas | |
| 2021/0113169 A1 | 4/2021 | Stango | |
| 2021/0228165 A1 | 7/2021 | Defreitas | |
| 2022/0087627 A1 | 3/2022 | Stango | |
| 2023/0233161 A1 | 7/2023 | DeFreitas | |
| 2023/0346329 A1 | 11/2023 | Stango | |
| 2023/0355190 A1 | 11/2023 | DeFreitas | |
| 2023/0363726 A1 | 11/2023 | Banks | |
| 2024/0245364 A1 | 7/2024 | Stango | |

FOREIGN PATENT DOCUMENTS

| | | |
|---|---|---|
| CN | 1738573 | 2/2006 |
| CN | 1810209 | 8/2006 |
| CN | 101766490 A | 7/2010 |
| CN | 102196772 | 9/2011 |
| CN | 102448375 | 5/2012 |
| CN | 102781328 | 11/2012 |
| CN | 103281961 | 9/2013 |
| CN | 104066374 | 9/2014 |
| CN | 105286904 A | 2/2016 |
| CN | 105637562 | 6/2016 |
| CN | 105769236 | 7/2016 |
| CN | 107170031 | 9/2017 |
| CN | 107518908 | 12/2017 |
| CN | 109893158 | 6/2019 |
| CN | 211432963 | 9/2020 |
| CN | 112004473 | 11/2020 |
| CN | 115348838 | 11/2022 |
| EP | 955886 | 11/1999 |
| EP | 1004274 A1 | 5/2000 |
| EP | 2341832 B1 | 7/2014 |
| EP | 2943125 B1 | 9/2018 |
| GB | 2545641 | 6/2017 |
| JP | S53-103672 | 8/1978 |
| JP | H03-86154 | 4/1991 |
| JP | H05-076409 U | 3/1992 |
| JP | 2003-525681 | 9/2003 |
| JP | 2004-261306 | 9/2004 |
| JP | 2005-523043 | 8/2005 |
| JP | 2006-212427 | 8/2006 |
| JP | 2007-135704 | 6/2007 |
| JP | 2008-518722 A | 6/2008 |
| JP | 2009-526618 A | 7/2009 |
| JP | 2009-219656 | 10/2009 |
| JP | 8-215172 | 3/2010 |
| JP | 2011-072667 | 4/2011 |
| JP | 2011-206436 | 10/2011 |
| JP | 2011-206438 | 10/2011 |
| JP | 2011-206439 | 10/2011 |
| JP | 2011-212111 | 10/2011 |
| JP | 2011-224351 | 11/2011 |
| JP | 2011-250842 | 12/2011 |
| JP | 2012-125536 | 7/2012 |
| JP | 2012-170718 | 9/2012 |
| JP | 2012-228404 | 11/2012 |
| JP | 2013017491 | 1/2013 |
| JP | 2014-068884 | 4/2014 |
| JP | 2014-068885 | 4/2014 |
| JP | 2015-027382 | 2/2015 |
| JP | 2016-022061 | 2/2016 |
| JP | 2016-517740 | 6/2016 |
| KR | 10-2011-0089446 | 8/2011 |
| KR | 10-2014-0058066 | 5/2014 |
| NL | 2020910 B1 | 11/2019 |
| NO | 2019/004821 | 1/2019 |
| NO | 2019/088826 | 5/2019 |
| WO | 2004/030523 | 4/2004 |
| WO | 2006/050466 | 5/2006 |
| WO | 2010/028208 | 3/2010 |
| WO | 2010/102087 | 9/2010 |
| WO | 2011/058730 | 5/2011 |
| WO | 2014/059366 | 4/2014 |
| WO | 2014/074602 | 5/2014 |
| WO | 2014/176445 A2 | 10/2014 |
| WO | 2015/054518 | 4/2015 |
| WO | 2016/073445 | 5/2016 |
| WO | 2018/067005 | 4/2018 |
| WO | 2018/089118 | 5/2018 |
| WO | 2018/170265 | 9/2018 |
| WO | 2019/227042 | 11/2019 |
| WO | 2019/227044 | 11/2019 |
| WO | 2019/227051 | 11/2019 |
| WO | 20190227042 | 11/2019 |
| WO | 20190227044 | 11/2019 |

OTHER PUBLICATIONS

PCT International Search Report and Written Opinion in International Application PCT/US2021/013716, mailed Jun. 28, 2021, 24 pages.
Digital Clinical Reports, Tomosynthesis (GE Brochure 98-5493, Nov. 1998), 8 pgs.
European Extended Search Report in Application 15857678.5, dated Jun. 26, 2018, 8 pages.
Grant, D.G., "Tomosynthesis: a three-dimensional imaging technique", IEEE Trans. Biomed. Engineering, vol. BME-19, #1, (Jan. 1972), pp. 20-28.
PCT International Preliminary Report on Patentability in International Application PCT/US2015/058782, dated May 18, 2017, 10 pgs.
PCT International Preliminary Report on Patentability in International Application PCT/US2017/053311, mailed May 14, 2019, 14 pgs.
PCT International Preliminary Report on Patentability in International Application PCT/US2018/046304, mailed Feb. 11, 2020, 14 pgs.
PCT International Preliminary Report on Patentability in International Application PCT/US2018/046312, mailed P/Nov. 2020, 12 pgs.
PCT International Search Report and Written Opinion of the International Searching Authority for corresponding International Patent Application No. PCT/US2015/058782 dated Feb. 17, 2016, 14 pgs.
PCT International Search Report and Written Opinion of the International Searching Authority for International Patent Application No. PCT/US2017/053311 mailed Mar. 6, 2018, 21 pages.
PCT International Search Report and Written Opinion of the International Searching Authority for International Patent Application No. PCT/US2018/046304 mailed Dec. 11, 2018, 18 pages.
PCT International Search Report and Written Opinion of the International Searching Authority for International Patent Application No. PCT/US2018/046312 mailed Dec. 11, 2018, 14 pages.
U.S. Appl. No. 60/628,516 entitled "Matching geometry generation and display of mammograms and tomosynthesis mages", filed Nov. 15, 2004, 20 pgs.
European Extended Search Report in Application 18843590.3, mailed Mar. 25, 2021, 9 pages.

(56) References Cited

OTHER PUBLICATIONS

Japanese Rejection in Application 2019-521374, mailed Jul. 26, 2021, 5 pages.
PCT International Search Report and Written Opinion in International Application PCT/IB2018/056208, mailed Nov. 13, 2018, 12 pages.
PCT International Preliminary Report on Patentability in International Application PCT/IB2018/056208, mailed Feb. 27, 2020, 10 pages.
European Communication and Search Report in Application 18847121.3, mailed Apr. 8, 2021, 5 pages.
European Extended Search Report in Application 18843788.3, mailed Mar. 29, 2021, 16 pages.
European Extended Search Report in Application 22183201.7, mailed Dec. 5, 2022, 7 pages.

* cited by examiner

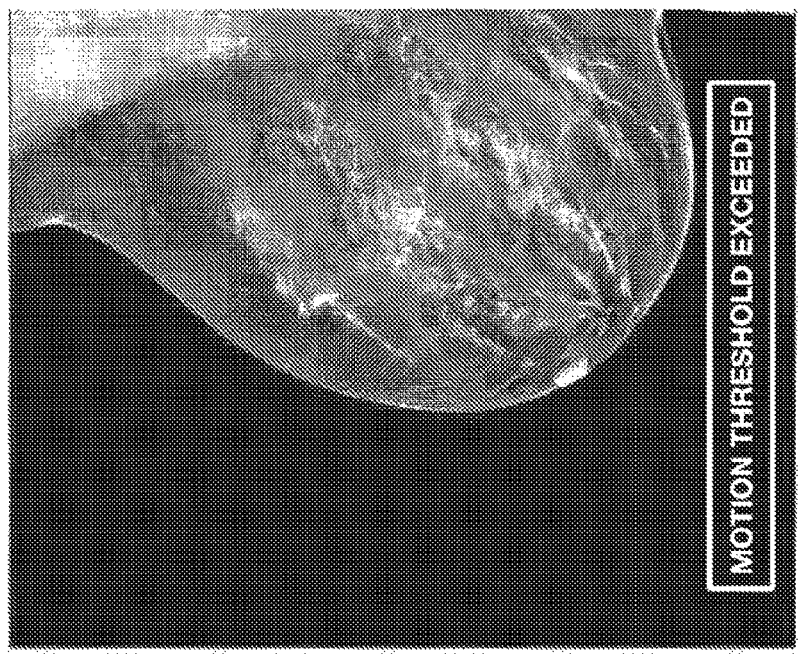

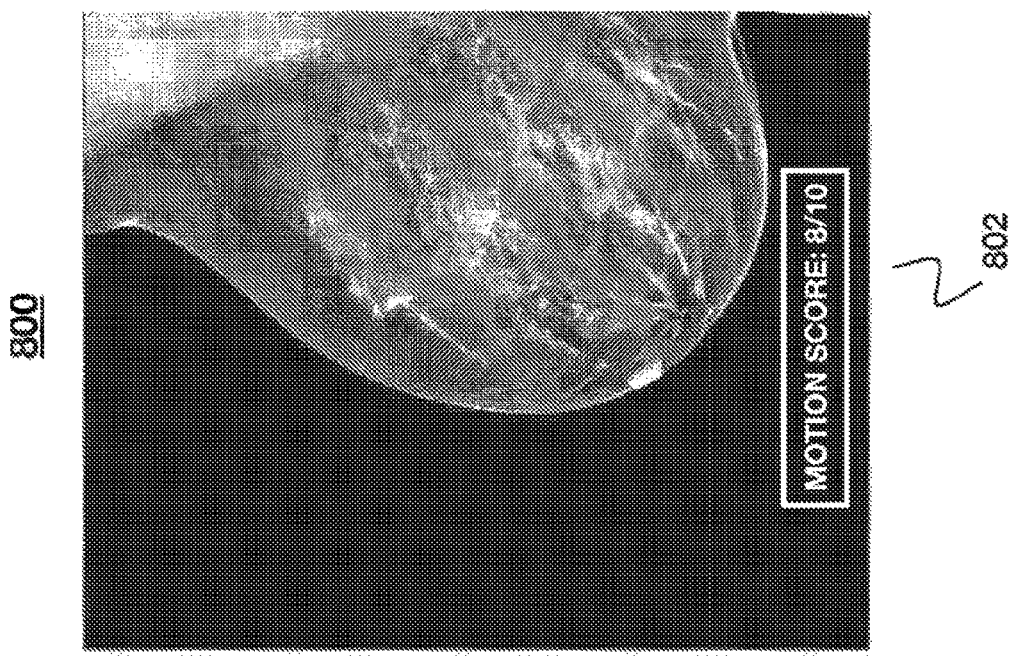

814

```
┌─────────────────────────────────────────────────────────────┐
│ RECEIVE ONE OR MORE SCORES FROM ONE OR MORE TECHNICIANS AT  │
│   A FIRST FACILITY AND ONE OR MORE SCORES FROM A SECOND     │
│                         FACILITY                            │
│                           804                               │
└─────────────────────────────────────────────────────────────┘
                              │
                              ▼
┌─────────────────────────────────────────────────────────────┐
│                     GENERATE REPORT                         │
│                           806                               │
└─────────────────────────────────────────────────────────────┘
                              │
                              ▼
┌─────────────────────────────────────────────────────────────┐
│                      COMPARE SCORES                         │
│                           810                               │
└─────────────────────────────────────────────────────────────┘
                              │
                              ▼
┌─────────────────────────────────────────────────────────────┐
│  IF SCORE IS ABOVE THRESHOLD, RECOMMEND CORRECTIVE ACTION   │
│                 FOR TECHNICIAN OR FACILITY.                 │
│                           812                               │
└─────────────────────────────────────────────────────────────┘
```

```
┌─────────────────────────────────────────────────────────────┐
│ RECEIVE, FROM A FIRST IMAGING FACILITY, A FIRST SET OF      │
│ QUALITY METRICS FOR A PLURALITY OF MEDICAL IMAGES ACQUIRED  │
│ AT THE FIRST IMAGING FACILITY                               │
│ 830                                                         │
└─────────────────────────────────────────────────────────────┘
                              ↓
┌─────────────────────────────────────────────────────────────┐
│ RECEIVE, FROM A SECOND IMAGING FACILITY, A SECOND SET OF    │
│ QUALITY METRICS FOR A SECOND PLURALITY OF MEDICAL IMAGES    │
│ ACQUIRED AT THE SECOND IMAGING FACILITY                     │
│ 832                                                         │
└─────────────────────────────────────────────────────────────┘
                              ↓
┌─────────────────────────────────────────────────────────────┐
│ COMPARE THE FIRST SET OF QUALITY METRICS TO THE SECOND SET  │
│ OF QUALITY METRICS                                          │
│ 834                                                         │
└─────────────────────────────────────────────────────────────┘
                              ↓
┌─────────────────────────────────────────────────────────────┐
│ BASED ON THE COMPARISON OF THE FIRST SET OF QUALITY METRICS │
│ TO THE SECOND SET OF QUALITY METRICS, GENERATING A          │
│ BENCHMARK FOR AT LEAST ONE METRIC                           │
│ 836                                                         │
└─────────────────────────────────────────────────────────────┘
                              ↓
┌─────────────────────────────────────────────────────────────┐
│ PROVIDE DASHBOARD TO FACILITY/FACILITIES TO REVIEW          │
│ AGGREGATED QUALITY METRICS                                  │
│ 838                                                         │
└─────────────────────────────────────────────────────────────┘
                              ↓
┌─────────────────────────────────────────────────────────────┐
│ GENERATE A TRAINING RECOMMENDATION BASED ON THE GENERATED   │
│ BENCHMARK                                                   │
│ 840                                                         │
└─────────────────────────────────────────────────────────────┘
                              ↓
┌─────────────────────────────────────────────────────────────┐
│ SEND THE GENERATED TRAINING RECOMMENDATION                  │
│ 842                                                         │
└─────────────────────────────────────────────────────────────┘
                              ↓
                           ( 8F )
```

FIG. 8E

MOTION, COMPRESSION, AND POSITIONING CORRECTIONS IN MEDICAL IMAGING

RELATED APPLICATIONS

This application is a continuation-in-part of International Application PCT/IB2018/056208, with an international filing date of Aug. 16, 2018, which claims priority to U.S. Provisional Patent Application Ser. No. 62/546,167, titled "Techniques for Breast Imaging Patient Motion Artifact Compensation" and filed on Aug. 16, 2017. The contents of the aforementioned applications are incorporated herein by reference in their entireties and, to the extent appropriate, priority is claimed to the aforementioned applications.

FIELD OF THE DISCLOSURE

The disclosure generally relates to quality assurance of patient imaging, and more particularly to improving detection of movement and correction of motion artifacts, such as it relates to mammography or tomosynthesis image acquisition.

BACKGROUND

Preventing movement of subject tissue, and in particular breast tissue, is important when performing radiation-based imaging of a patient for a variety of reasons. First, some imaging procedures last for a non-trivial period of time, and movement during a portion of the procedure may negatively impact image quality. Specifically, patient motion may cause anatomical distortions or artifacts, which can be exaggerated during longer exposure times. Second, it is desirable to minimize a patient's total exposure to radiation during a procedure and, thus, subsequent imaging to obtain proper image quality is not ideal. Third, due to regulations in many jurisdictions, subsequent imaging used solely to correct image quality may be counted against a practitioner or organization, and frequent re-imaging may result in revocation of a license and/or accreditation. Fourth, poor quality images due to excess movement may require a patient to make subsequent visits to an imaging center, placing additional burden on the patient and the healthcare system itself, including the imaging center and payer.

SUMMARY

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

Techniques for detecting and/or otherwise notifying a patient of detected motion and modifying the imaging protocol during breast imaging are described. As described above, preventing movement breast tissue, is important when performing radiation-based imaging of a patient for a variety of reasons including improving image quality, improving patient experience, reducing exposure and avoiding repeat imaging. For at least these reasons, there is a need for improved techniques, which may be automated or semi-automated, for detection of movement during an imaging procedure, for corrective actions during and after the procedure when movement has been detected, and for minimizing the amount of radiation exposure to patients in a workflow efficient manner.

An imaging system as described herein may include an imaging detector to capture an image of human tissue, such as breast tissue, and a compression paddle situated apart from the imaging detector to compress the human tissue between the compression paddle and the imaging detector. One or more sensors may be included, in one embodiment a force sensor may generate a force signal indicating a measure of force applied to the human tissue. A movement detection circuit may filter a movement signal from the force signal indicating a measure of movement of the compressed human tissue. A movement analysis module may determine that the movement signal is beyond a movement threshold. An image correction module may perform a corrective action based upon the determination that the movement signal is beyond a movement threshold. Other embodiments are described and claimed.

The force sensor described herein is typical to most modern mammography systems where breast compression force is incorporated. The force sensor helps to prevent excessive compression of the patient's breast which can cause pain and other undesirable effects. The embodiments as described and claimed relate to the output of the force sensor, representative of a force level, which may be filtered or converted by one or more circuits or modules described herein into a value that indicates movement. This movement signal, when compared to other measurements over time, may indicate movement of the patient undergoing an imaging procedure.

In addition or in the alternative, other sensors may be used. For example, one or more ultrasound sensors, optical and/or infrared sensors may be used. In some examples, the sensors may be located either in a grid on the compression paddle. In other examples, the sensors may be located on the periphery of the paddle. The sensors may capture spatial data information from the compression of the breast. The special information may be used to create motion maps and/or contact maps. The motion map information can be used to create a correction map. The correction map information may be used as input to the image correction algorithm which corrects the tomosynthesis images. In the examples where a contact map is created based on the spatial information, the contact map can be used to create compression contours, which can be used as an input to the compression adequacy analysis and recommend a corrective action.

Some software based techniques for detecting motion during an imaging procedure have been previously described. For example, one method of detecting patient motion includes detecting from a series of images displacement of an edge line such as the skin line of the breast, an implant edge, or some other internal edge. This skin line detection process is disclosed in U.S. Pat. No. 9,498,180, titled System and Method For Detecting Patient Motion During Tomosynthesis Scans, which is incorporated by reference herein (hereafter the '180 Patent).

However, unlike software based and image artifact based motion detection, detection of motion based on hardware sensors gives an objective measure of patient motion to add to the assessment of motion. The independent, hardware based, detection using the information from one or more sensors allows for greater accuracy. In addition, because the mammography system already includes the force sensor, this method of patient motion is more cost effective than the alternative image based detection when force sensor detection is used. In addition, different types of motion may be detected and different compensation actions may be taken. For example, if motion with regular movement interval is detected, such as breathing or heartbeat, image capture may be synchronized with the motion. In a different example, if irregular movement is detected, such as patient adjusting position, the image capture may be delayed. Such nuanced and continued detection may not be possible if the detection is based on image processing alone.

In an aspect, the present technology relates to an imaging system that includes a breast compression paddle, an imaging detector, at least one sensor incorporated into at least one of the breast compression paddle or the imaging detector, at least one processor, and memory, operatively coupled to the at least one processor, storing instructions that when executed by the at least one processor, cause the system to perform a set of operations. The set of operations includes generating, at a first time point, first spatial data of the breast based on data captured by the at least one sensor; generating, at a second time point, second spatial data of the breast based on data captured by the at least one sensor; based on the first spatial data and the second spatial data, determining an amount of motion of the breast that occurred between the first time point and the second time point; and based on the determined amount of motion performing at least one of: generating a motion map for the breast; discarding one or more acquired projections for use in generating a tomosynthesis reconstruction; or correcting a medical image acquired at substantially the second time point.

In an example, the at least one sensor includes at least one of an optical sensor, an infrared sensor, or an ultrasonic sensor. In another example, the at least one sensor includes a set of sensors incorporated into the breast compression paddle and the imaging detector. In yet another example, the motion map includes magnitudes of motion for a plurality of different regions of the breast. In still another example, the operations further include, based on the determined amount of motion, generating a correction map. In a further example, the operations further include comparing the determined amount of motion to a predetermined threshold; and discarding one or more acquired projections is based on the comparison. In still yet another example, at least one sensor is an ultrasound sensor, and the first spatial data includes data of internal breast tissue.

In another aspect, the technology relates to an imaging system including a breast compression paddle; an imaging detector; at least one sensor incorporated into at least one of the breast compression paddle or the imaging detector; at least one processor; and memory, operatively coupled to the at least one processor, storing instructions that when executed by the at least one processor, cause the system to perform a set of operations. The set of operations includes generating, based on data captured by the at least one sensor, spatial data for a breast compressed between the breast compression paddle and the imaging detector; generating, based on the spatial data, at least one of a contact map or positional data for the compressed breast; and based on the at least one of a contact map or positional data, generating a notification that the breast is in an at least one of an improper compression or an improper position.

In an example, the at least one sensor includes at least one of an optical sensor, an infrared sensor, or an ultrasonic sensor. In another example, the at least one sensor includes a set of sensors incorporated into the breast compression paddle and the imaging detector. In yet another example, the contact map includes a skin line for the breast, an uncompressed breast line, and a roll-off region between the uncompressed breast line and the skin line. In still another example, the operation further comprise, based on the contact map, determining a value for the roll-off region; comparing the determined value for the roll-off region to a predetermined threshold for the roll-off region; and the notification is generated based on the comparison. In a further example, the value for the roll-off region is at least one of an area of the roll-off region, a maximum distance between the uncompressed breast line and the skin line, a minimum distance between the uncompressed breast line and the skin line, or a ratio between the area of the roll-off region and an area of the breast in contact with the at least one of the breast compression paddle or the imaging detector. In yet another example, the positional data includes data based on the position of a pectoral muscle.

In another aspect, the technology relates to a method implemented by an imaging system. The method includes generating, at a first time point, first spatial data of a breast based on data captured by at least one sensor incorporated into at least one of a breast compression paddle or an imaging detector; generating, based on the first spatial data, at least one of a contact map or positional data for the compressed breast; and based on the at least one of a contact map or positional data, generating a notification that the breast is in at least one of an improper compression or an improper position.

In an example, the method further includes generating, at a second time point, second spatial data of the breast based on data captured by the at least one sensor; based on the first spatial data and the second spatial data, determining an amount of motion of the breast that occurred between the first time point and the second time point; and based on the determined amount of motion performing at least one of: generating a motion map for the breast; discarding one or more acquired projections for use in generating a tomosynthesis reconstruction; or correcting a medical image acquired at substantially the second time point.

In an example, the method further includes comparing the determined amount of motion to a predetermined threshold; and wherein discarding one or more acquired projections is based on the comparison. In another example, the method further comprises based on the contact map, determining a value for a roll-off region; comparing the determined value for the roll-off region to a predetermined threshold for the roll-off region; and wherein the notification is generated based on the comparison. In yet another example, the value for the roll-off region is at least one of: an area of the roll-off region, a maximum distance between an uncompressed breast line and a skin line of the breast, a minimum distance between the uncompressed breast line and the skin line, or a ratio between the area of the roll-off region and an area of the entire breast. In a further example, the at least one sensor includes at least one of an optical sensor, an infrared sensor, or an ultrasonic sensor.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

BRIEF DESCRIPTION OF THE DRAWINGS

FIG. 7 illustrates a generated image according to an embodiment.

FIG. 8A illustrates a generated image according to an embodiment.

FIG. 8C illustrates a logic flow according to an embodiment.

FIG. 8E illustrates a logic flow according to an embodiment.

DETAILED DESCRIPTION

Figure 1:
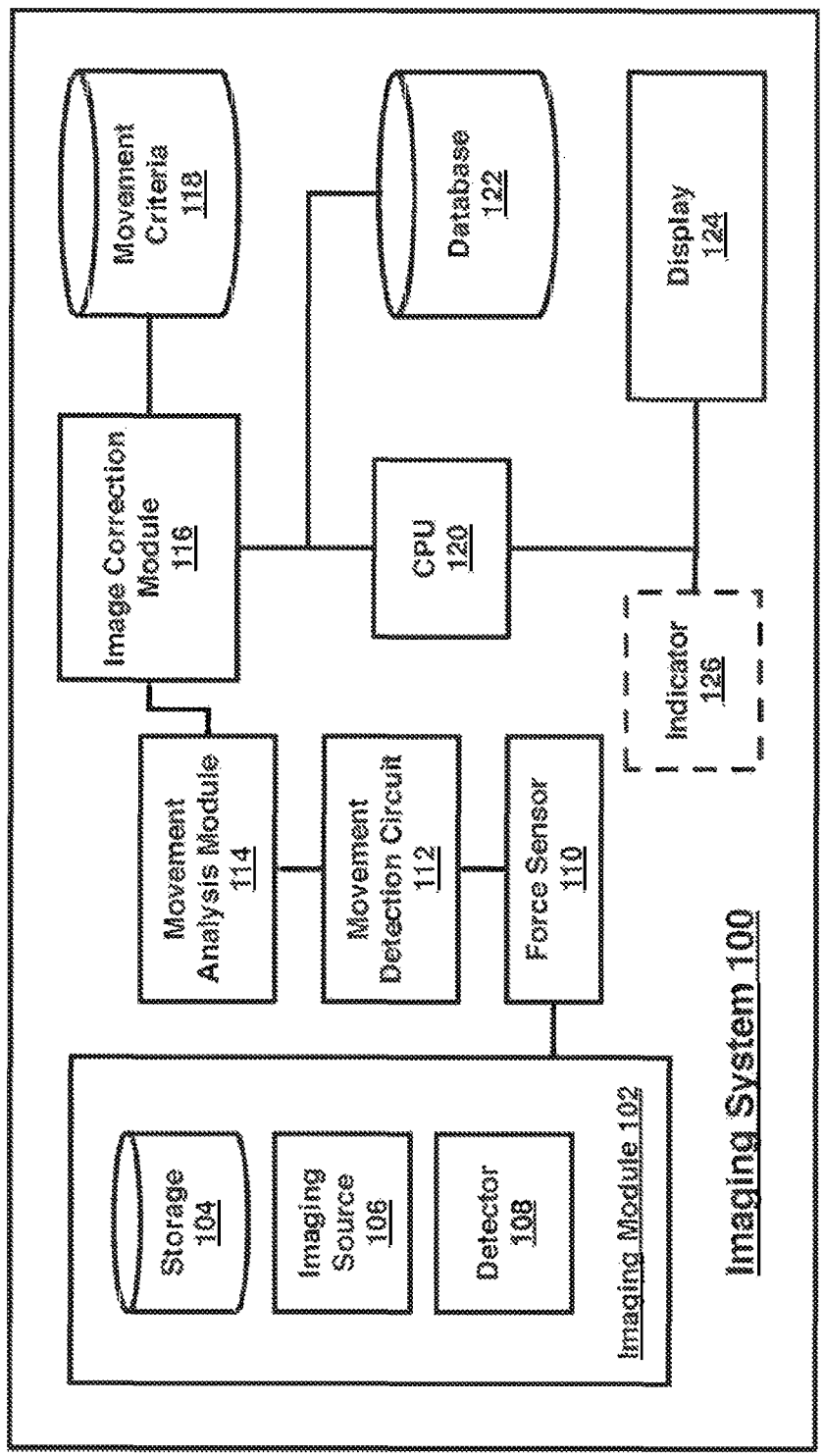
FIG. 1 illustrates an embodiment of an imaging system.

Techniques for breast imaging patient motion compensation, compression evaluation, and positioning evaluation are described. An imaging system may include an imaging detector to capture an image of human tissue, such as breast tissue or other soft tissue, and a compression paddle situated apart from the imaging detector to compress the human tissue between the compression paddle and the imaging detector. In one embodiment, a force sensor may generate a force signal indicating a measure of force applied to the human tissue. A movement detection circuit may filter a movement signal from the force signal indicating a measure of movement of the compressed human tissue. A movement analysis module may determine that the movement signal is beyond a movement threshold. An image correction module to perform a corrective action based upon the determination that the movement signal is beyond a movement threshold. In another embodiment, other types of sensors may be used which may be disposed in a grid or around the periphery of the compression paddle.

As used herein, corrective actions may include actions to correct an image, generate an image while minimizing motion artifacts, generate an audio or visual indication that motion has been detected, and/or other actions described below in response to detection of motion during a procedure. By way of example and not limitation, corrective actions may include the determination and display of a movement score on a display device, display of an alert on a display device indicating that a movement threshold has been exceeded, triggering a visual indicator of the imaging system, terminating or modifying an imaging sequence or imaging protocol or image acquisition, delaying capture of the image of human tissue until the movement threshold is no longer exceeded, and/or synchronizing an image capture with repetitive movement. A movement score for all images taken by a particular technologist may be combined to create a positioning score for the technologist. The movement scores may be compared to other technologists in a facility or in other facilities. The technologist score may be compared to a threshold to determine compliance. A facility score may be compared to other facilities and compared to a threshold score to determine compliance. A report may be generated showing positioning scores for the technologist, the facility and compliance over time. A retrospective and prospective approach will allow the facility to identify the root-cause for why the positioning, noise, artifacts, compression etc. at the physician level could occur. A particular technician can be identified with this approach to understand his/her behavior to improve their ability to take their image. Other embodiments are described and claimed.

With general reference to notations and nomenclature used herein, the detailed descriptions which follow may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

FIG. 1 illustrates a block diagram for an imaging system 100. In one embodiment, the imaging system 100 may comprise one or more components. Although the imaging system 100 shown in FIG. 1 has a limited number of elements in a certain topology, it may be appreciated that the imaging system 100 may include more or less elements in alternate topologies as desired for a given implementation. The imaging system 100 may include a plurality of modules, including imaging module 102, movement analysis module 114, and image correction module 116, which may each include one or more processing units, storage units, network interfaces, or other hardware and software elements described in more detail herein. In some embodiments, these modules may be included within a single imaging device, utilizing shared CPU 120. In other embodiments, one or more modules may be part of a distributed architecture, an example of which is described with respect to FIG. 11.

In an embodiment, each module of imaging system 100 may comprise without limitation an imaging system, mobile computing device, a smart phone, or a desktop computer, or other devices described herein. In various embodiments, imaging system 100 may comprise or implement multiple components or modules. As used herein the terms "component" and "module" are intended to refer to computer-related entities, comprising either hardware, a combination of hardware and software, software, or software in execution. For example, a component and/or module can be implemented as a process running on a processor, such as CPU 120, a hard disk drive, multiple storage drives (of optical and/or magnetic storage medium), an object, an executable, a thread of execution, a program, and/or a computer. By way of illustration, both an application running on a server and the server can be a component and/or module. One or more components and/or modules can reside within a process and/or thread of execution, and a component and/or module can be localized on one computer and/or distributed between two or more computers as desired for a given implementation. The embodiments are not limited in this context.

The various devices within system 100, and components and/or modules within a device of system 100, may be communicatively coupled via various types of communications media as indicated by various lines or arrows. In various embodiments, the various modules and storages of system 100 may be organized as a distributed system. A distributed system typically comprises multiple autonomous computers that communicate through a computer network. It is worthy to note that although some embodiments may utilize a distributed system when describing various enhanced techniques for data retrieval, it may be appreciated that the enhanced techniques for data retrieval may be implemented by a single computing device as well. The embodiments are not limited in this context.

In an embodiment, imaging module 102 may include an imaging source 106 and a detector 108, which may be used to perform breast imaging (2D, tomosynthesis, computed tomography, ultrasound or any combination thereof), and may be an x-ray source and detector in some examples. In other examples, imaging source 106 and detector 108 may be other types of imaging sources and sensors, respectively. For example, in some embodiments imaging module 102 may be configured to perform breast imaging, such as x-ray mammography, tomosynthesis, computed tomography, and/or ultrasound. Tomosynthesis is a method for performing high-resolution limited-angle tomography at radiographic dose levels. While mammography is used as an exemplary embodiment through the description, it can be appreciated that the techniques described herein may be applicable to other procedures in which imaging of human tissue susceptible to movement may occur.

Imaging source 106 may be configured to expose human tissue, such as breast tissue, to x-rays, which may be detected by detector 108. Detector 108 may be configured to respond to the influence of incident x-rays over a wide range. Detector 108 may be configured to absorb x-rays, produce an electronic signal, digitize the signal, and store the results in one of storage 104 and/or database 122. The output image may be saved as a two-dimensional matrix, where each element represents the x-ray transmission corresponding to a path through the breast tissue. Three-dimensional images and matrices may be generated in some embodiments, depending on the imaging modality, such as tomosynthesis, computed tomography, and the like. The image may be digitally processed such that when it is displayed on a display device or printed on laser film, it will illustrate the key features required for diagnosis. Such diagnostic images may be stored in storage 104 so that they may be viewed on a user interface of display 124.

In an embodiment, images may also be archived in image database 122. In this manner, patient records may be maintained and past images may be used to evaluate detected movement when compared to new images. In an exemplary embodiment, an image correction module, described herein, may refer to archived images containing common elements (e.g., still calcification for the same tissue of the same patient) and compare to a current image (which may include blurry calcifications for the same tissue of the same patient). Such as analysis, combined with the techniques described herein, may be used to detect and/or correct motion artifacts within an image.

Figure 2:
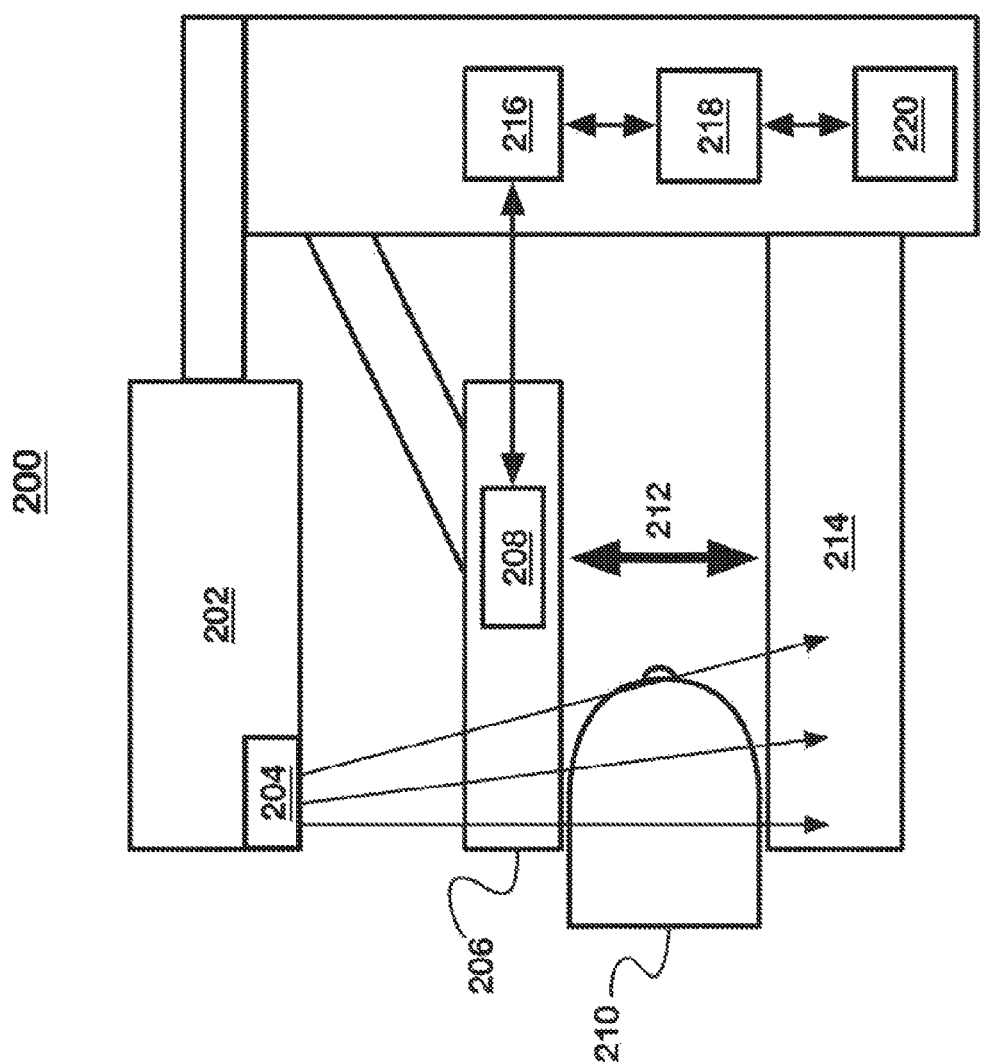
FIG. 2 illustrates an embodiment of an imaging system.
Figure 3:
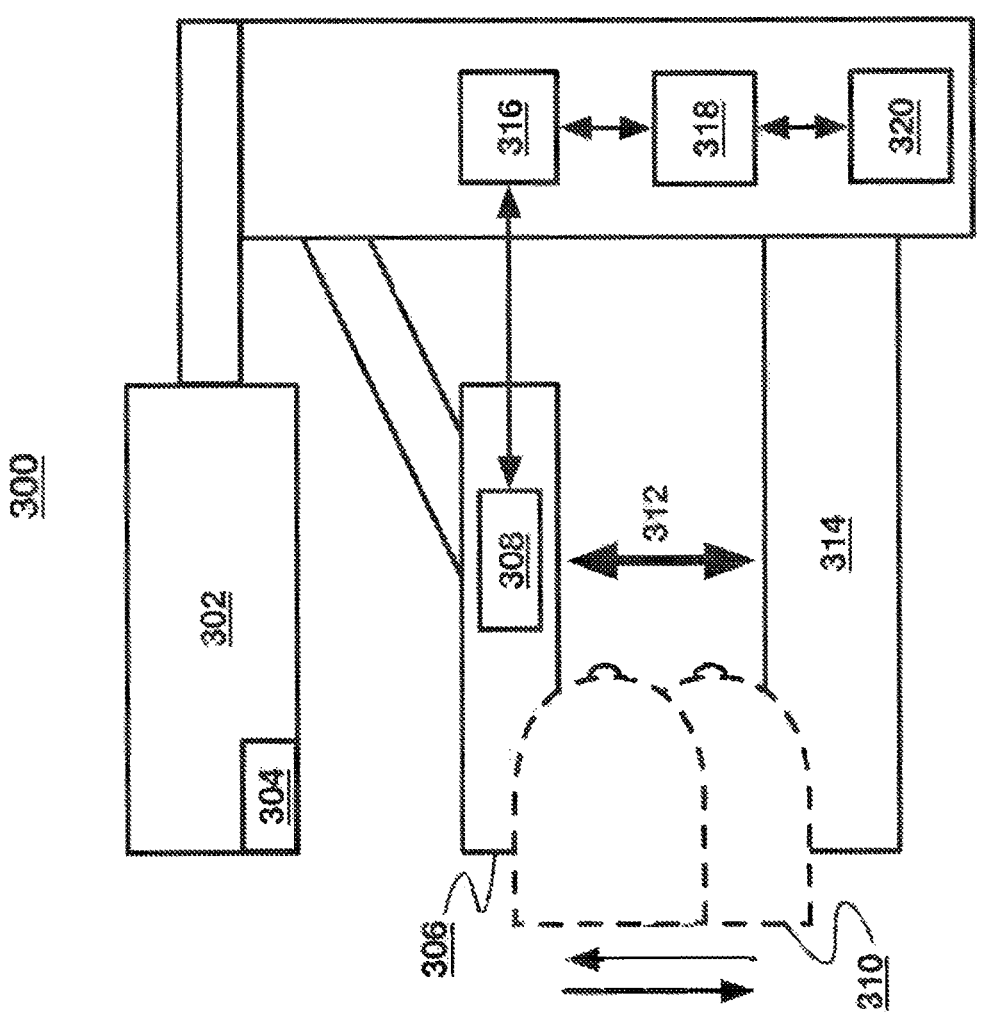
FIG. 3 illustrates an embodiment of an imaging system.

Imaging system 100 may include a force sensor 110, which may be contained within a compression paddle of imaging system 100 (not shown in FIG. 1, illustrated in FIGS. 2 and 3). Force sensor 110 may include a strain gauge, piezoelectric sensor, load cell, or other sensor capable of measuring the force applied to human tissue compressed between a compression paddle and an opposite detector plane. In some embodiments, force sensor 110 may include an analog filter, gain circuits for signal conditioning, and/or an analog-to-digital converter for signal capture. The output of force sensor 110 may be an electrical signal representative of a force level. The force level may represent a measurement of force applied superior to the breast via the compression paddle and/or via the imaging detector "top" surface. The electrical signal representative of a force level may be filtered or converted by one or more circuits or modules described herein into a value that indicates movement. This movement signal, when compared to other measurements over time, may indicate movement of the patient undergoing an imaging procedure.

Imaging system 100 may include a movement detection circuit 112, configured to receive an electronic force signal from force sensor 110 and filter a movement signal from the received force signal In some embodiments, the received force signal may include a low frequency compression force signal (e.g., 0 (DC) to <5 Hz), which may be tapped and processed in parallel using movement detection circuit 112. Movement detection circuit 112 may include one or more components to process and filter the force signal, including a DC signal block, such as a blocking capacitor to remove the DC and low frequency components of the force signal, leaving a higher frequency (AC) component, referred to herein as a movement signal One or more analog circuits may filter and apply gain to the higher frequency (AC) signal components to improve signal-to-noise ratio, if needed. The resulting movement signal may include motion artifacts from the original force signal. As described later, one or more modules, such as movement analysis module 114 may include a digital processing unit and corresponding software to analyze the output from movement detection circuit 112.

In an embodiment, a movement analysis module 114 may include one or more analog circuits, such as a tuned differentiator, to detect movement of human tissue compressed within imaging system 100 using a received movement signal from movement detection circuit 112. In some embodiments, movement analysis module 114 may include hardware and/or software modules configured to accept the movement signal from movement detection circuit 112, and detect tissue movement caused by the patient. An exemplary logic flow illustrating movement detection by movement analysis module 114 is set forth within FIG. 4. By way of example and not limitation, movement may be caused by respiratory activity, cardiac activity, or muscular movements (voluntary or involuntary) by the patient. Movement analysis module 114 may be configured with a movement threshold value, beyond which, movement of the patient is detected and communicated to an image correction module 116.

Image correction module 116 may be configured to receive a determination from movement analysis module 114 that movement has been detected. The determination may include data indicating a movement time and movement level in some embodiments, and the determination may be used to determine a corrective action to be taken. Techniques described herein strive to improve image quality, even in situations where movement is detected, reduce patient radiation exposure when possible, and reduce the time required for patients to undergo imaging procedures. Exemplary corrective actions are described herein with respect to FIGS. 5, 7, and 8 however, other corrective action may be taken consistent with these goals, in some embodiments.

A database of movement criteria 118 may be used by image correction module 116 to determine the proper corrective action based upon various determinations by movement analysis module 114. For example, criteria within movement criteria database 8 may include movement thresholds, time thresholds for delay, image quality criteria, thresholds indicating the maximum number of images that can be deleted from an image sequence due to detected movement, and other criteria necessary to determine and take corrective actions. In an example, image correction module 116 may include hardware and/or software configured consistent with the techniques described herein to take one or more corrective actions when movement exceeding a threshold has been detected. As described further with respect to FIG. 5, certain movement determinations may be handled in different ways. In an embodiment, image improvements may be made by deleting images associated with movement above a threshold. In an embodiment, an image capture procedure may be delayed until detected movement has fallen below a threshold. In an embodiment, an image capture procedure may be extended so that a proper exposure can be taken while also excluding images from an imaging sequence impacted by movement. In an embodiment, an image capture procedure may be canceled, reducing patient radiation exposure.

In some embodiments, artifact-based image detection of patient motion as described in the '180 Patent, may be combined with the information from the force sensor 110 and the movement detection circuit 112 in the movement analysis module 114. In one example, the movement analysis module 114 may correlate the information received from the motion detection circuit with the artifact based image detection.

In an embodiment, display device 121 may include a user interface configured to receive and display an image along with information with respect to detected movement and any corrective actions taken in response. In an embodiment, display 124 may be configured to display an alert or movement score (FIGS. 7 and 8) indicating to a practitioner that movement was detected and/or a level of detected movement. Optionally, imaging system 100 may include an indicator 126, which may include an LED, that may be triggered when movement exceeding a threshold has been detected during a procedure. In addition to a notification via the user interface of display 124 or optional indicator 126, other techniques for notification of detected movement may be used. Non-limiting examples include audio notification, haptic notification, other visual indication using lights, and/or one or more prompts within the user interface.

FIG. 2 illustrates an imaging system 200 according to an embodiment. Imaging system 200 illustrates exemplary components most relevant to the techniques described herein and may include other components not depicted within FIG. 2. Upper portion 202 including imaging source 204, which may he an x-ray source in some embodiments and may be consistent with imaging source 106, described above with respect to FIG. 1.

Compression paddle 206 may be mounted to an arm, itself connected to a frame connected to a body of the imaging system 200. Compression paddle 206 may be lowered onto human tissue during an imaging procedure. Certain imaging procedures, such as mammography, may require compression of human tissue between compression paddle 206 and another surface, such as the surface of detector 214, which may be consistent with detector 108, described above with respect to FIG. 1.

Force sensor module 208 may be contained within compression paddle 206, and may detect force 212 imparted on breast 210, which is placed between compression paddle 206 and imaging detector 214. The detected force may represent a measurement of force applied superior to the breast via the compression paddle 206 and/or via the imaging detector 214 "top" surface. Additionally or separately, a force sensor module may be incorporated into the imaging detector 214 component. In this configuration, the force sensor module incorporated into the imaging detector 214 may operate in the same manner as the force sensor module 208 and may measure the DC and AC compression signals applied by the compression paddle 206 upon the human tissue (breast 210) that is placed between the compression paddle 206 and upon the surface of the imaging detector 214. As set forth above, force sensor 208, or the optional force sensor incorporated into the imaging detector 214, may include a strain gauge, piezoelectric sensor, load cell, or other sensor capable of measuring the force applied to human tissue compressed between a compression paddle and an opposite detector plane, in some embodiments, force sensor 208, or the optional force sensor incorporated into the imaging detector 214, may include an analog filter, gain circuits for signal conditioning, and/or an analog-to-digital converter for signal capture. The output of force sensor 208, or the optional force sensor incorporated into the imaging detector 214, may be an electrical signal representative of a force level, which may be filtered or converted by one or more circuits or modules described herein into a value that indicates movement. This movement signal, when compared to other measurements over time, may indicate movement of the patient undergoing an imaging procedure.

In an embodiment, the described force sensor modules may include one or more circuitry components comprising a movement detection circuit, such as movement detection circuit 112. In an embodiment, movement detection circuit 216 may be implemented separate from force sensor 208, and may receive a signal therefrom. As described with respect to FIG. 1, movement detection circuit 216 may receive a force signal from force sensor 208 and filter a high-frequency AC component from the received force signal into a movement signal indicating movement of the human tissue compressed between compression paddle 206 and a surface of detector 214.

Movement analysis module 218, which may be implemented in hardware and/or software, may be configured to determine whether a received movement signal has exceeded a movement threshold. In some embodiments, the movement analysis module 28 may be present separate from force sensor 208, and may be within, the optional force sensor incorporated into the imaging detector 214, compression paddle 206 or within another portion of imaging system 200, as illustrated. If a movement threshold has been exceeded, movement analysis module may communicate that determination to image correction module 220, which may be configured to take corrective action, as described herein with respect to FIGS. 5, 7, and 8.

FIG. 3 illustrates an imaging system 200 according to an embodiment. Elements within FIG. 3 may be similar to like-numbered elements from FIG. 2. The key difference between FIG. 2 and FIG. 3 is the illustration of movement of breast 310. As illustrated, breast 310 may be moved while between compression paddle 306 and a surface of detector 314. This movement may affect a force measurement 312 made by force sensor 308. While a generally up and down movement is illustrated within FIG. 3, it can be appreciated that a variety of movements may be made by breast 310. Movement may be due to a variety of factors, such as relating to cardiac or respiratory movements, sneezing, or voluntarily or involuntarily moving one or more portions of the body that affect the movement of breast 310. As described below, movement of breast 310 may be of any number of types, and may be temporally evaluated by one or more modules of imaging system 300. Evaluation of movement type and movement timing using techniques described herein may provide increased image quality and patient experience while reducing patient exposure to radiation.

As discussed above, patient motion during a breast imaging procedure can adversely affect imaging quality and therefore the diagnostic value of the resultant images. Detecting and/or measuring motion and correction, however, is difficult due at least in part to the fact that the breast is a non-rigid object. Accordingly, motion patterns of the breast during the imaging procedure may be complex in both time and space. For instance, some portions of the breast may move differently from other portions. As a result, image quality may change for different regions of a breast image. For a modality such as tomosynthesis, the motion or movement may occur between acquiring projections and/or during exposure of one or more of the projections.

Proper compression and positioning of the breast during the imaging procedure also affects image quality. Inadequate compression of the breast may increase the likelihood of unwanted results. For example, inadequate compression may increase the likelihood of motion, which reduces image quality. As another example, inadequate compression may increase the likelihood of overlapping tissue which may make it more difficult to detect cancerous lesions in a resultant image. Thus, there is a need to more accurately detect motion and compression in space and time, which can prove to be useful input data to help correct and enhance image quality during breast imaging procedures.

Figure 14A:
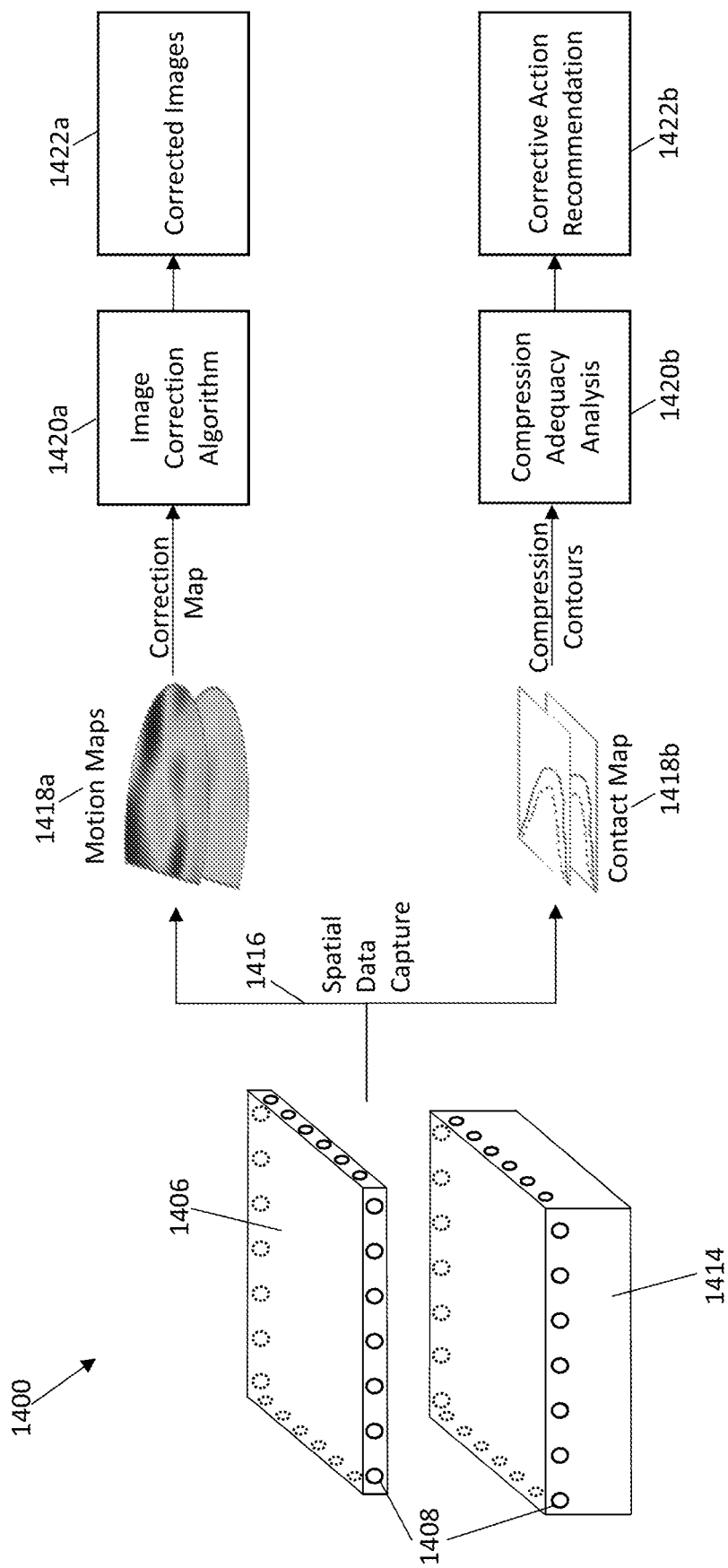
FIG. 14A illustrates an embodiment of an imaging system.

FIG. 14A illustrates another embodiment of an imaging system 400 where one or more sensors, in combination or alternatively to the force sensor 208, are used. Elements within FIG. 14A may be similar to like-numbered elements from FIG. 1, FIG. 2, and/or FIG. 3. Imaging system 1400 illustrates exemplary components most relevant to the techniques described herein and may include other components not depicted with FIG. 14. The imaging system 1400 includes a compression paddle 1406 and a detector 1414 disposed a distance away from and parallel to the compression paddle. A breast is compressed between the compression paddle 1406 and the detector 1414. While referred to herein as the detector 1414, the detector 1414 may be considered the housing surrounding the detector, such as a breast platform. Accordingly, in some examples, discussion of the detector 1414 may be synonymous with discussion of the breast platform or the structure housing or surrounding the actual electronics that detect x-ray beams passing through the breast.

One or more sensors 1408 are disposed on or within the compression paddle 1406 and the detector 1414. The one or more sensors 1408 may comprise or communicate with a sensor module which may detect motion of the breast and may also be used to detect or analyze compression and positioning of the breast. In one example, the sensors 1408 may include one or more photo sensors, infrared sensors and/or ultrasound or ultrasonic sensors. The motion detected by the sensors 1408 may be based on reflected sonic signals and/or reflected light signals depending on the types of sensors 1408 implemented. For example, the photo sensors may include cameras to capture optical images of the breast when it is in a compressed and/or uncompressed state. Similarly, the infrared sensors may be utilized to produce a three-dimensional image or depth map of the breast that may be used to determine the three-dimensional location of exterior of the breast at different points in time. The ultrasound or ultrasonic sensors may also be used to detect the three-dimensional location of the exterior of the breast. In some examples, the ultrasound or ultrasonic sensors may also be utilized to image the interior of the breast. With the interior of the breast imaged, landmarks within the breast may be identified and the locations of those landmarks may be tracked in three-dimensional space at different points in time.

In some embodiments, the sensors 1408 may be placed in a grid pattern on or within the compression paddle 1406 and the detector 1414. In other examples, the sensors 1408 may be disposed around the periphery of the compression paddle 1406 and the detector 1414. The location and pattern of the sensors may be based on the types of sensor and the physical properties of the compression paddle 1406 and/or the detector 1414. For example, if the compression paddle 1406 is optically opaque, the photo sensors may be placed in a position where they have a line of sight to the exterior of the breast that is not blocked by the compression paddle 1406. Similarly, for some ultrasound or ultrasonic sensors, an air gap between the sensor and the breast may be undesirable. As such, the ultrasonic sensors may be placed in location where there is no air gap between the ultrasonic sensor and the breast. Other solid surfaces, such as a portion of the compression paddle 1406 and/or detector 1414 may still be located between the ultrasonic sensor and the compressed breast.

By disposing multiple sensors in a pattern, a more detailed understanding of motion of the breast may be obtained. It is appreciated that movement of the breast may not be uniform. For example, some areas of the breast may move more than others. Use of multiple sensors allows the imaging system 1400 to create a motion map that may be capable of visually showing the location of movement throughout the surface of the breast. In other examples, the motion map may not be a visual representation but rather a set of data indicating the locations of the breast that moved as well as the magnitude and direction of the breast movement at each location. For instance, the motion map may be a set of motion vectors for different positions in three-dimensional space. By having a more complete understanding of the location of motion of the breast, the imaging system can determine whether the motion may have had a negative effect on the image obtained. In addition, having additional sensors allows the imaging system to obtain other information such as the amount of contact with the breast, as further discussed below, to determine breast positioning and compression information.

The sensors 1408 that may be incorporated into the imaging detector 1414 and/or the compression paddle 1406 may include an analog filter, gain circuits for signal conditioning, and/or an analog-to-digital converter for signal capture. The output of sensors 1408 may be electrical signals representative of motion and/or spatial data representative of location of the breast, which may be filtered or converted by one or more circuits or modules described herein into a plurality of spatial information or data 1416. The spatial information may be combined to create a motion map 1418*a*. The motion map 1418*a* takes spatial information from each of the sensors 1408 to create a relative representation of motion. The motion map 1408*a* may describe some areas of the breast that include more motion than others. The motion map 1408*a* may be a visual representation of the spatial information having some colors (e.g. red) represent higher amount of motion and other colors represent moderate (e.g. yellow) or low (e.g. green) amount of motion. The relative representation of motion may be determined based on spatial information comparison to a threshold or a look up table representing various levels of motion. In other examples, the motion map 1418*a* may not include a visual representation but rather a set of data indicating the locations of the breast that moved as well as the magnitude and direction of the breast movement at each location. For instance, the motion map 1418*a* may be a set of motion vectors for different positions in three-dimensional space.

In addition, the motion map 1408*a* may be created for each of the tomosynthesis projections or slices created. For example, FIG. 14A shows two tomosynthesis projections. One projection has a larger degree of motion and another projection showing smaller degree of motion. It is appreciated that any number of motion maps 1408*a* may be created based on the number of projections. As an example, spatial data representative of the breast may be captured by the sensors 1408 during different times during the imaging procedure. For instance, the spatial data may be captured at substantially the same time as when a projection is captured. The spatial data may also be captured by the sensors 1408 continuously or substantially continuously. Accordingly, a change in position or location of the breast (or a portion thereof) between the capture of the projections may be determined. Such a change in position or location may be indicative of motion of the breast (or a portion thereof). Based on the magnitude of the motion, particular projections may be discarded when generating a tomosynthesis reconstruction of the breast. In other examples, the projections may be corrected prior to or during generation of the tomosynthesis reconstruction of the breast.

The information or data from the motion map 1418*a* may be provided as input into an image correction module or algorithm 1420*a*. In some examples, the motion map 1418*a* may be utilized to generate a correction map. That correction map may effectively be an inverse of the motion map 1418*a*. For instance, the correction map may indicate how pixels in the image should be adjusted based on the detected motion. The image correction module or algorithm 1420*a* may be similar to the image correction modules 116 and 220 described above with respect to FIGS. 1, 2, and 3, and may perform the functions and correction as further described with reference to FIGS. 4 and 5. The image correction algorithm 1420*a* may then output corrected images 1420*a*.

Figure 14B:
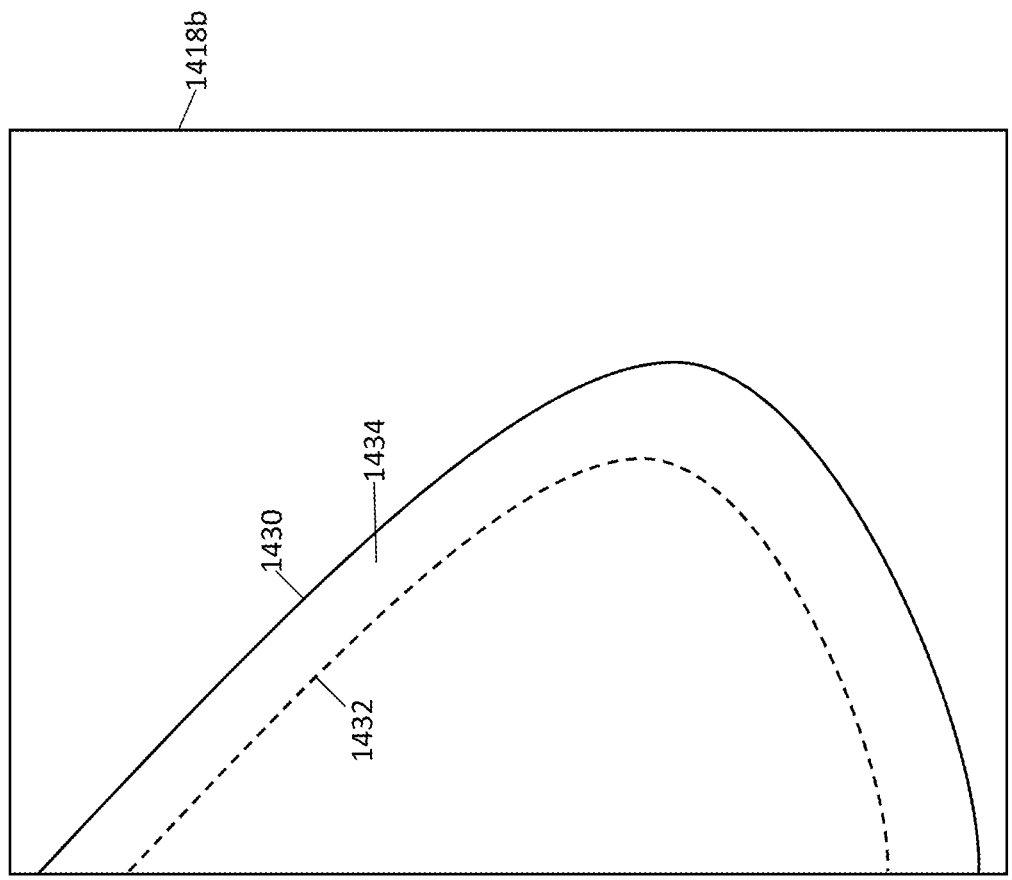
FIG. 14B illustrates an example contact map according to an embodiment.

The spatial information 1416 may also be used to create a contact map 1418*b*. An example of a contact map 1418*b* is depicted in FIG. 14B. It is appreciated by inventors that the entirety of the breast 1410 is not in contact with the compression paddle 1406 and the detector 1414 when the breast is compressed. For example, when the breast is compressed between the paddle 1406 and the detector 1414, a portion of breast near the periphery of the breast is not in contact with either the paddle 1406 or the detector 1414. There may be a line 1432, referred to as the "uncompressed tissue line" or the "paddle contact line" in an image, which defines a contour of contact points of breast with paddle/detector. The contact map 1418*b* may also display the breast profile or skin line 1430 of the image of the breast. The location of uncompressed tissue line 1432 with respect to breast profile or skin line 1430 may also be used to give a metric of the adequacy of the compression and/or positioning of the compressed breast. For example, the larger the area of uncompressed tissue, the less adequate the compression. It is further appreciated by the inventors that a less than adequate level of compression may result in poor image quality.

The contact map 1418*b* shows or indicates the level of contact with the breast. The contact map 1418*b* can be used to determine or define a roll-off region 1434, which is the region where the breast is uncompressed. The roll-off region 1434 may be the area between the uncompressed tissue line 1432 and the skin line 1430 of the breast. The size of the roll-off region 1434 may be represented by the area between the uncompressed tissue line 1432 and the skin line 1430. The size of the roll-off region 1434 may also be represented by a distance between the uncompressed tissue line 1432 and the skin line 1430. The distance may be the maximum, minimum, and/or average distance between the uncompressed tissue line 1432 and the skin line 1430. The location of the uncompressed tissue line 1342 and the size of the roll off region 1434 may also be useful in special image processing techniques in uncompressed versus compressed breast areas. The location of uncompressed tissue line 1432 with respect to breast profile 1430 may also be used to give an idea of how adequate the compression is, which may also be used in determining the adequacy of positioning of the breast.

Additional positioning information of the breast may also be determined from the data produced by the sensors 1408. For example, in a mediolateral oblique (MLO) compression, the sensors may be used to determine whether the pectoral muscle is properly positioned such that it will be imaged during the imaging procedure. The spatial data produced by the sensors 1408 may also be used to assess the alignment of the nipple, such as by determining the posterior nipple line (PNL). Other positioning criteria may also be determined from the spatial data produced by the sensors 1408.

Returning to FIG. 14A, the information from the contact map 1418b and/or the other positioning information may be input in a compression adequacy analysis module or algorithm 1420b. The compression adequacy analysis module 1420b may be similar to the image correction modules 116 and 220, with the difference of that a threshold of compression is used, rather than a motion threshold, to compare the current compression contours to the threshold of compression contours. The compression adequacy analysis module 1420b may perform at least some of the functions and corrections as further described with reference to FIGS. 4, 5, and 15A-C. As an example, the compression adequacy analysis may include comparing the area for the roll-off region to a threshold for the area of the roll-off region. For example, if current compression contours are below a threshold for the compression contours, image capture may be delayed until contours are above the threshold, or image capture may be cancelled if the delay exceeds a threshold. In at least one example, one or more alerts or alarms as discussed above may be generated to notify the technologist that compression is inadequate and the patient may need to be repositioned. Accordingly, determinations regarding whether compression and/or positioning of the breast are proper may be made prior to the patient being exposed to a dose of x-ray radiation.

Included herein is a set of flow charts representative of exemplary methodologies for performing novel aspects of the disclosed architecture. While, for purposes of simplicity of explanation, the one or more methodologies shown herein, for example, in the form of a flow chart or flow diagram, are shown and described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

Figure 15A:
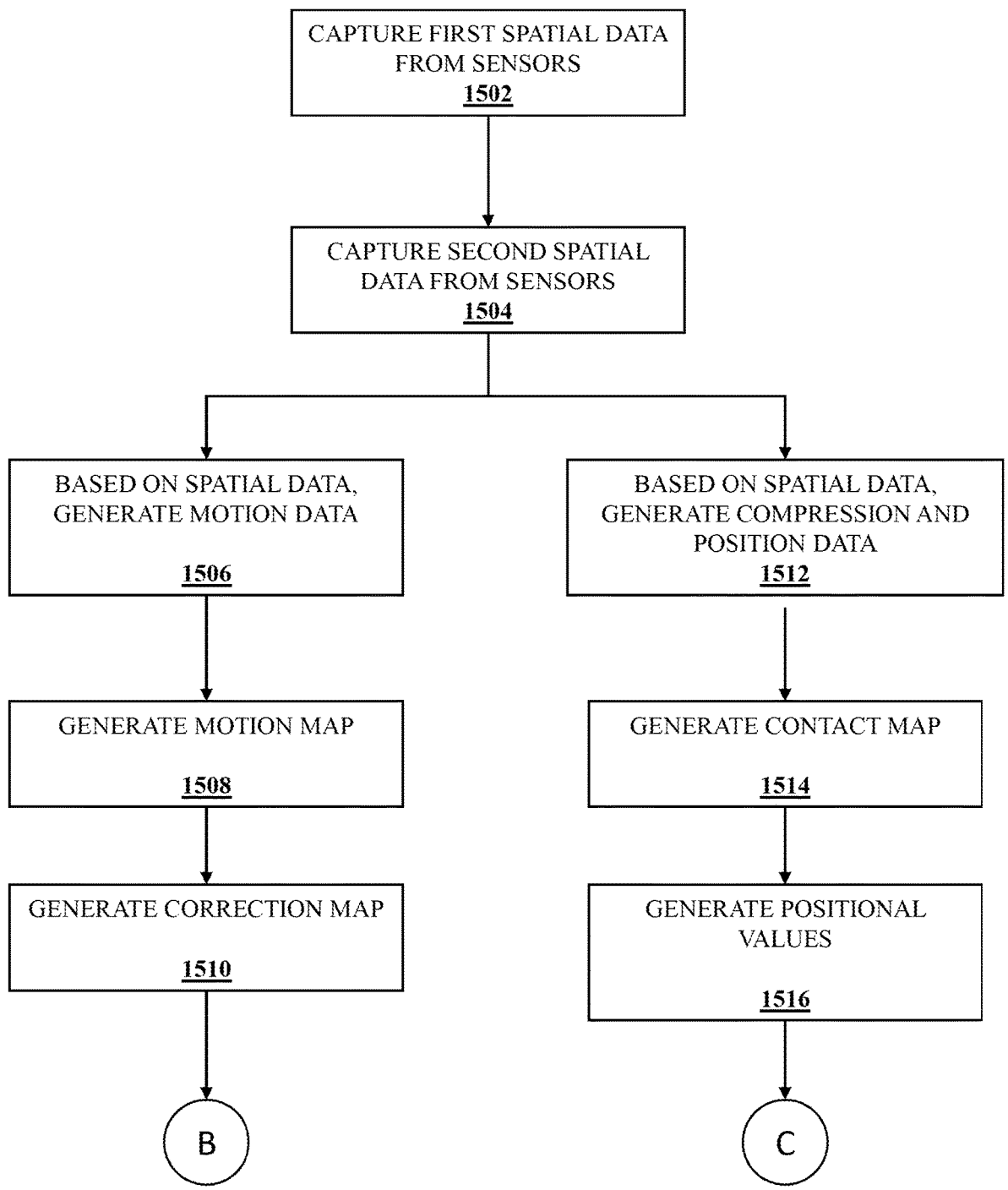
FIGS. 15A-C illustrate a logic flow according to an embodiment.
Figure 15B:
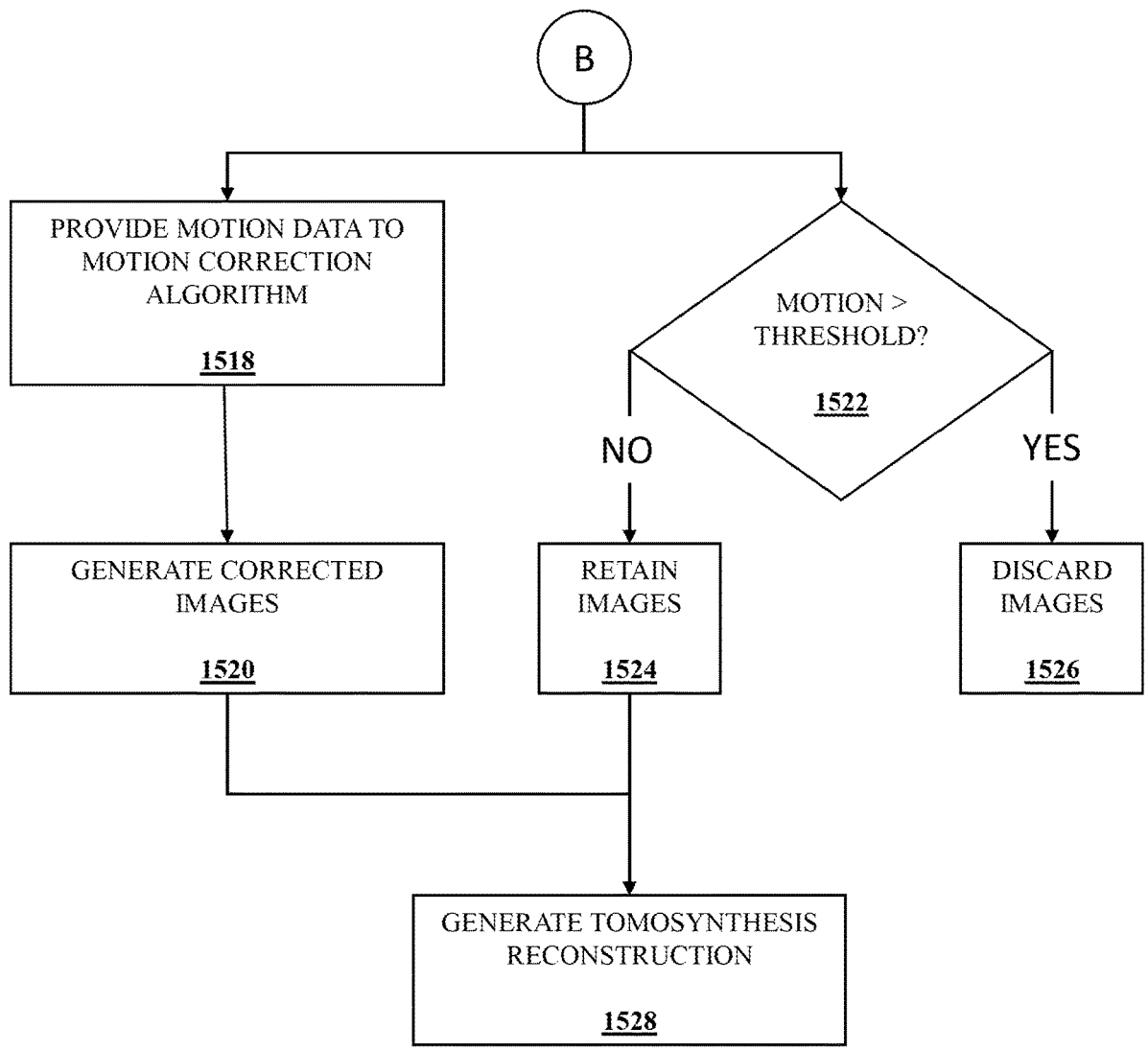
Figure 15C:
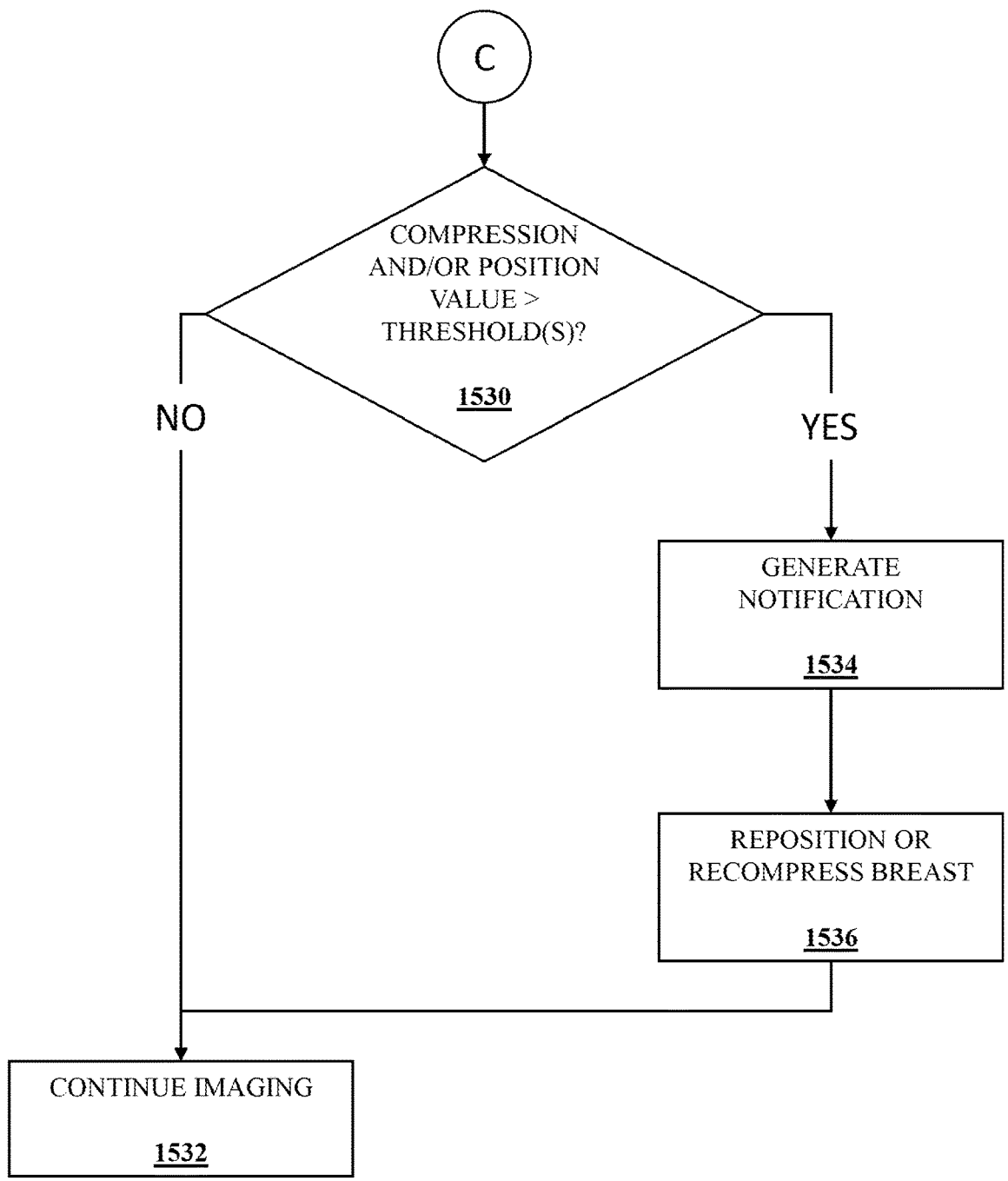

FIGS. 15A-C illustrate a logic flow 1500 according to an embodiment. The logic flow 1500 may be representative of some the operations executed by one or more embodiments described herein, such as imaging system 100, for example. At operation 1502, a first set of spatial data of the breast is generated at a first time point based on data captured by the sensors that may be incorporated into at least one of the breast compression paddle and/or the imaging detector. At operation 1504, a second set of spatial data of the breast is generated at a second time point based on data captured by the sensors. The spatial data of the breast at each time point may be representative of the location of the breast at the respective time point. The spatial data may be three-dimensional data about the exterior and/or interior of the breast. The time points may also coincide with the acquisitions of projections in tomosynthesis imaging procedure as well as time points prior to any x-ray exposures during the imaging procedure. For example, the first time point may be after compression but prior to the first exposure. The second time point may coincide with the first projection. While only two time points are depicted in logic flow 1500, it should be appreciated that additional spatial data may be captured or generated at additional time points. For example, spatial data may be generated at a third time point coinciding with the capture of a second projection. The spatial data may also be continuously or substantially continuously generated and captured during the imaging procedure.

At operation 1506, motion data may be generated based on the first set of spatial data and the second set of spatial data. For example, by comparing the first spatial data to the second spatial data, a difference in location of the breast or portions of the breast may be determined. That change in location corresponds to motion. The generated motion data may indicate an amount of motion that occurred for the breast or a portion of the breast. Generating motion data may also include generating a motion map at operation 1508. The motion map, for example, may be a visual representation of the spatial information having some colors represent higher amount of motion and other colors represent moderate or low amount of motion. At operation 1510, a correction map may be generated from or based on the motion map. That correction map may effectively be an inverse of the motion map. For instance, the correction map may indicate how pixels in the image should be adjusted based on the detected motion.

The motion data generated in operation 1506 may also be utilized for motion correction or tomosynthesis reconstruction, as shown in FIG. 15B. At operation 1518, the motion data may be provided as an input into a motion correction algorithm. For example, the motion map and/or the correction map may be provided to the motion correction algorithm. The motion correction algorithm then corrects at least one medical image based on the input of the motion data to generate one or more corrected medical images in operation 1520. For example, if the second spatial data is generated for a time point that coincides with the capture of a medical image, the motion data may be used to correct that medical image. Accordingly, the image correction algorithm may correct a medical image acquired at substantially the second time point. Using a tomosynthesis procedure as an example, the first spatial data and a first projection may be captured at the first time point and the second spatial data and a second projection may be captured at the second time point. The motion data may then be used to correct the second projection prior to the projections being used to generate a tomosynthesis reconstruction at operation 1528. While only two projections are discussed in the example, it should be understood that such corrections may be applied to any of number of projections captured during a tomosynthesis imaging procedure.

The motion data for each of the projections or medical images may also be compared to a predetermined motion threshold at operation 1522. For example, an amount of motion that occurred between a first projection and a second projection may be compared to a motion threshold. If the amount of motion that occurred between the projections is greater than a threshold, the projection or medical image may be discarded at operation 1526. For example, the second projection may be discarded if the amount of motion that occurred between the first and second projection is greater than the predetermined motion threshold. The thresholds described herein may be dynamic or predetermined. For example, the thresholds may be dynamically determined by an imaging system during the image capture process based, at least in part, on a detected image quality assessment taken in near real-time. In other embodiments, a movement threshold may be predetermined and stored within an imaging system. The predetermined thresholds discussed herein may be a setting or a value that is stored or accessed by the medical imaging system or a portion thereof. For instance, the predetermined thresholds may be set by a medical professional, be provided with the imaging system, or accessed from a remote source. The thresholds may be based on values, percentages, ratios, or other types of thresholds.

If, however, the motion amount is not greater than the predetermined threshold, the projection or image is retained at operation 1524. The images or projections that are retained may then be used to generate a tomosynthesis reconstruction in operation 1528. In some examples, images that are discarded in operation 1526 may be regenerated through a synthesis or interpolation of other acquired projections. Those synthesized projections may then be used in generating the tomosynthesis reconstruction in operation 1528.

Returning to FIG. 15A, the spatial data captured in operation 1502 and/or operation 1504 may also be utilized to generate compression and position data in operation 1512. For example, the first spatial data captured in operation 1502 may be captured when the breast is compressed but prior to an x-ray exposure having occurred. Compression and/or position data may be generated for the breast that corresponds to that time of compression at operation 1512. Generating compression data may include generating a contact map for the compressed breast in operation 1514. Generation of the contract map may also include determining or generating values representative of the roll-off region. For example, a value for the area of the roll-off region or a distance representative of the roll-off region may be determined. The value for the roll-off region may be at least one of an area of the roll-off region, a maximum distance between the uncompressed breast line and the skin line, a minimum distance between the uncompressed breast line and the skin line, or a ratio between the area of the roll-off region and an area of the breast in contact with the at least one of the breast compression paddle or the imaging detector, among other possible values. Generating position information may include generating positional values for the breast at operation 1516. The positional values may include values for positioning metrics, such as a value for the posterior nipple line (PNL) or another value relating to the position of the pectoral muscle. Values for other positioning metrics may also be generated from the spatial data.

As shown in FIG. 15C, at operation 1530, the compression and/or position data generated in operations 1512-1516 may be compared to one or more threshold values. For example, with respect to compression, a value for the roll-off region of the breast may be compared to a predetermined threshold for that value. As an example relating to positioning data, a value for the PNL may be compared to a predetermined threshold value for the PNL. If the compression values and/or the positioning values do not exceed the thresholds (or are otherwise within a tolerance threshold), then imaging continues and the medical images, such as mammography or tomography images are acquired at operation 1532.

If the compression values and/or the positioning values do exceed the thresholds (or are outside of the tolerance thresholds), then a notification or alert may be generated in operation 1534. The notification may be a visual notification, such as a notification displayed on a screen or indicated by illumination of a light. The notification may also be an audible notification played through a speaker or other sound-making device. The notification may indicate that the compression is inadequate or improper and/or that the breast in improperly positioned. The notification may further indicate a reason as to why the compression was inadequate, such as too large of a roll-off area, and/or why the breast was improperly positioned, such as an improper PNL value. In addition, the notification may provide guidance to the medical professional or technician as to how the breast should be repositioned. At operation 1536, the breast may be repositioned or recompressed. Once the breast is repositioned or recompressed, the imaging procedure continues and medical images are acquired at operation 1532. In some examples, upon repositioning and/or recompressing the breast at operation 1536, method 1500 flows back to the start where spatial data is recaptured at operation 1502. The operations determining whether the positioning and/or compression is proper may then be repeated for the repositioned and/or recompressed breast until the breast is determined to be in a proper position and properly compressed.

Figure 4:
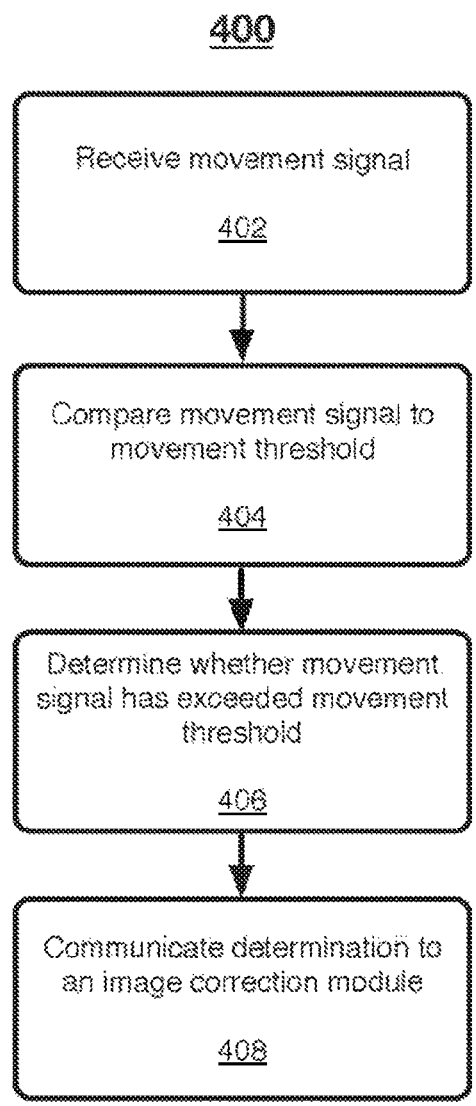
FIG. 4 illustrates a logic flow according to an embodiment.

FIG. 4 illustrates a logic flow 400 according to an embodiment. The logic flow 400 may be representative of some or all of the operations executed by one or more embodiments described herein, such as imaging system 100, for example. Specifically, logic flow 400 may illustrate operations performed by a movement analysis module, such as movement analysis module 114.

At 402, a movement analysis module may receive a movement signal from a force sensor and/or movement detection circuit. The movement signal may include motion artifacts indicating that human tissue, currently under compression during an imaging procedure, has moved. Using hardware and/or software components, the received movement signal may be evaluated to isolate data indicating movement and a value may be assigned indicating a movement level. In an embodiment, a baseline movement signal may be first evaluated, indicating a baseline movement value, or a baseline movement value may be stored within an imaging system. Subsequent movement signals may be received and compared to the baseline movement value to identify motion artifacts within the subsequent movement signals.

At 404, the movement analysis module may compare subsequently received movement signals, and any motion artifacts identified therein, to a movement threshold, which may be predetermined and stored within a non-transitory computer-readable storage medium. In some embodiments, thresholds may be dynamically determined by an imaging system during the image capture process based, at least in part, on a detected image quality assessment taken in near real-time. In other embodiments, a movement threshold may be predetermined and stored within an imaging system.

At 406, the movement analysis module may determine whether the received movement signal has exceeded the movement threshold and, at 408, the movement analysis module may communicate the determination to an image correction module, which is discussed in more detail below. The determination, in some embodiments, may include an indication that movement has been detected, a movement value, a timestamp, a frame identifier, or other information that may be necessary for an image correction module to take appropriate corrective measures based upon the detected movement.

Figure 5:
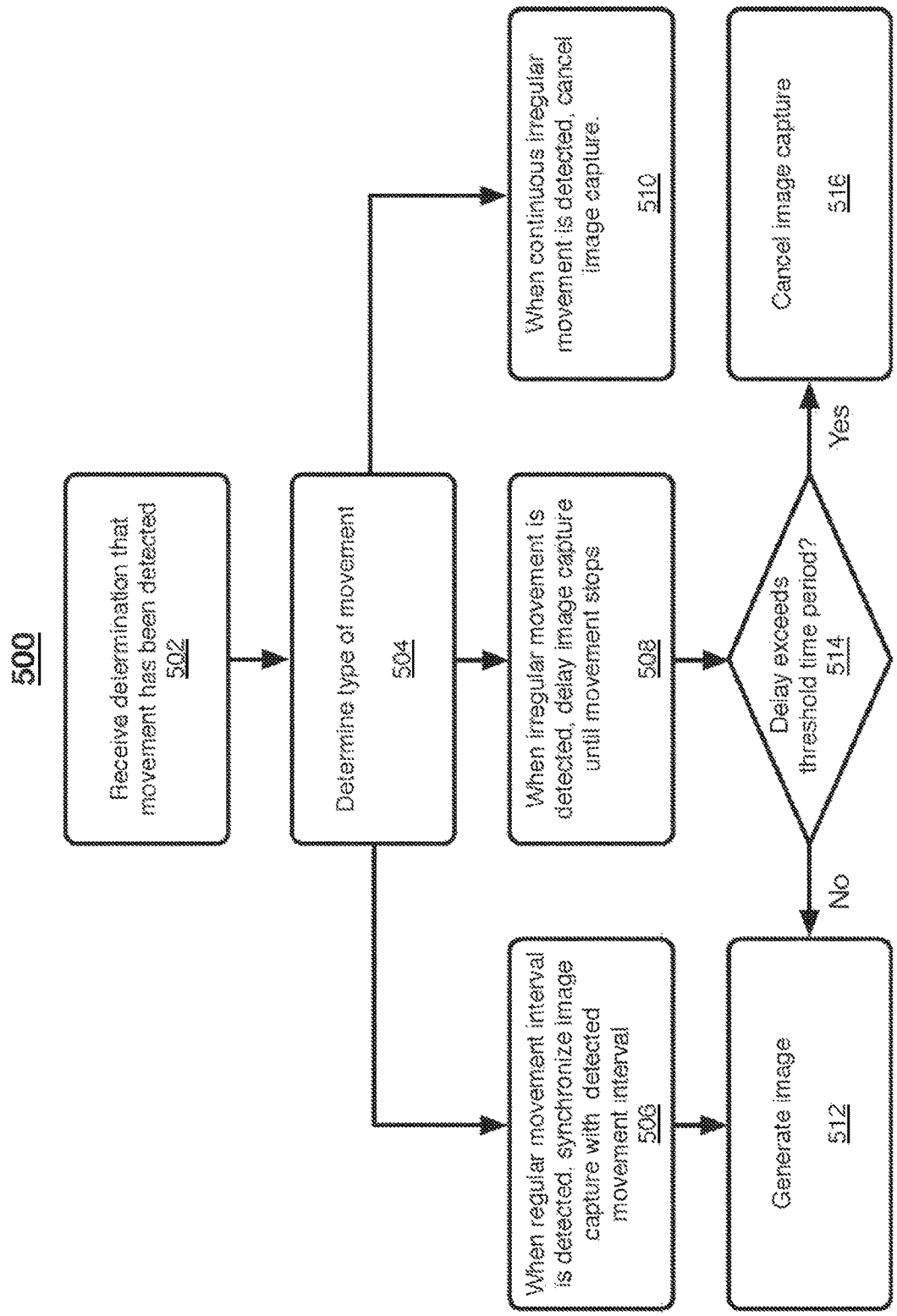
FIG. 5 illustrates a logic flow according to an embodiment.

FIG. 5 illustrates a logic flow 500 according to an embodiment. The logic flow 500 may be representative of some or all of the operations executed by one or more embodiments described herein, such as imaging system 100, for example. Specifically, logic flow 500 may illustrate operations performed by an image correction module, such as image correction module 116.

At 502, an image correction module may receive a determination that movement has been detected. In some embodiments, any movement may be communicated to the image correction module. In other embodiments, only movement that exceeds a threshold, as described herein, may be communicated to the image correction module. The determination, in some embodiments, may include an indication that movement has been detected, a movement value, a timestamp, a frame identifier, or other information that may be necessary for an image correction module to take appropriate corrective measures based upon the detected movement.

At 504, the image correction module may determine a type of movement based upon one or more received movement determinations. For example, a movement may be categorized as a regular movement when it is repetitive and generally within a regular time interval. This type of movement may indicate a patient is breathing, or moving in a regular fashion. In another example, movement may be categorized as irregular. A single irregular movement may indicate a patient has shifted positions, or sneezed, for example. In yet another example, movement may be categorized as continuously irregular. A determination of movement type may be based, in part, on a movement value and/or timestamp, for example. In at least one example, a determination of the movement may be that the movement is localized to one or more tomosynthesis slices.

At 506, when a regular movement that is repetitive and generally within a regular time interval is detected, the image correction module may configure the image capture to the synchronized with the regular movement. In this manner, image capture may he performed during a time period in which movement is not detected, and skipped during a time period in which movement is detected. The synchronized image sequence may be generated at 512, and may include only images in which movement has not been detected, or detected movement is below a threshold amount.

At 508, when irregular movement is detected, the image correction module may delay image capture for a period of time, allowing the movement to stop so an image is not negatively impacted. As described herein, some embodiments may flag image captured images taken during a movement, and those images may be removed from an imaging sequence used to generate an image.

At 510, if a termination of movement is localized to one or more tomosynthesis slices. The slices may be removed or cancelled from the tomosynthesis stack that are associated with movement above a threshold.

At 514, if irregular movements continue during the delay period, the delay may be extended until movement stops. However, since in some cases the patient may be exposed to x-ray radiation during the delay, a time period threshold may be set for which the image capture may be canceled if the delay lasts beyond the threshold. Thus, an image may be generated at 512 if the delay is within the time threshold, and the image capture may be canceled at 516 if the delay period extends beyond the time threshold. In this manner, an imaging system may be able to compensate for some movement, and generate higher quality images by delaying capture until movement is no longer detected, while at the same time canceling an image and limiting patient radiation exposure when a satisfactory image cannot be obtained due to excessive irregular movement.

During image generation at 512, certain embodiments may correlate images with detected movement and flag images in which movement was detected. In this manner, images flagged with movement may be removed from a resulting imaging sequence, thus, improving overall image quality despite detecting motion within the imaging procedure. In some cases, many images may be flagged as occurring during movement and the entire imaging sequence may need to be canceled. Based upon a particular procedure, for example, a threshold may be set such that an image correction module may determine whether the process of deleting images may result in a usable image sequence, or if the imaging sequence needs to be canceled due to excessive movement during the imaging procedure.

Figure 6:
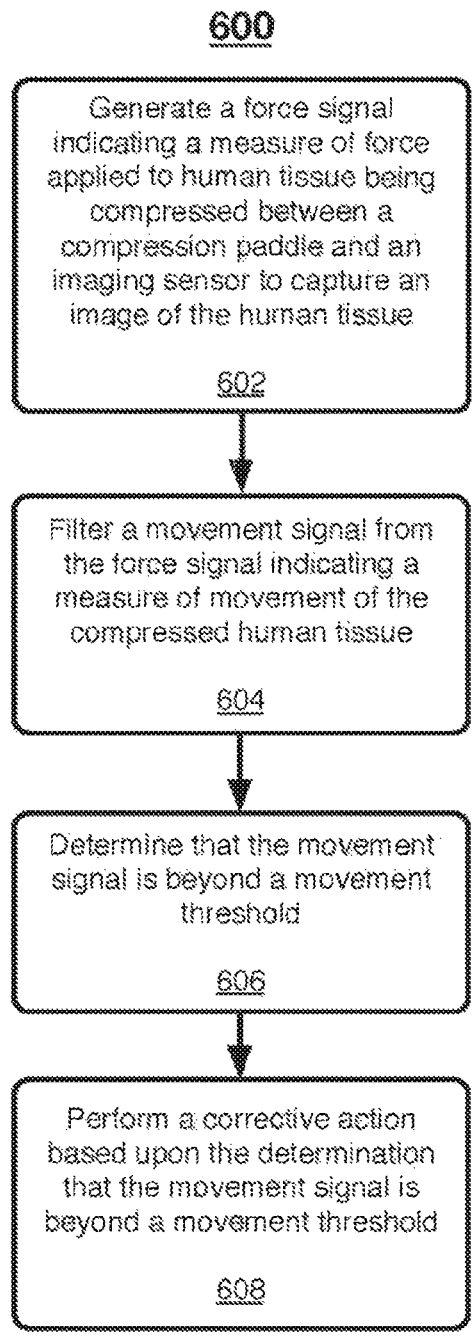
FIG. 6 illustrates a logic flow according to an embodiment.

FIG. 6 illustrates a logic flow 600 according to an embodiment. The logic flow 600 may be representative of some or all of the operations executed by one or more embodiments described herein, such as imaging systems 100, 200, and/or 300, for example. At 602, a force sensor may generate a force signal indicating a measure of force applied to human tissue being compressed between a compression paddle and an imaging detector to capture an image of the human tissue. As set forth above, a force sensor may include a strain gauge, piezoelectric sensor, load cell, or other sensor capable of measuring the force applied to human tissue compressed between a compression paddle and an opposite detector plane. In some embodiments, a force sensor may include an analog filter, gain circuits for signal conditioning, and/or an analog-to-digital converter for signal capture. The output of a force sensor may be an electrical signal representative of a force level, which may be filtered or converted by one or more circuits or modules described herein into a value that indicates movement. This movement signal, when compared to other measurements over time, may indicate movement of the patient undergoing an imaging procedure.

At 604, a movement detection circuit may filter the received force signal and isolate a movement signal from therein. The movement signal may indicate a level of force, and in some cases may indicate that a patient has moved during image capture in a manner that is detrimental to the quality of a resulting image. As set forth above, the movement detection circuit may be configured to receive an electronic force signal from a force sensor and filter a movement signal from the received force signal. In some embodiments, the received force signal may include a low frequency compression force signal (e.g., 0 (DC) to <5 Hz), winch may be tapped and processed in parallel using the movement detection circuit. Further, the movement detection circuit may include one or more components to process the force signal, including a DC signal block, such as a blocking capacitor to remove the DC and low frequency components of the force signal, leaving a higher frequency (AC) component, referred to herein as a movement signal. One or more analog circuits may filter and apply gain to the higher frequency (AC) signal components to improve signal-to-noise ratio, if needed. The resulting movement signal may include motion artifacts from the original force signal.

At 606, a movement analysis module may determine whether a detected movement is beyond a movement threshold. The movement analysis module may include one or more analog circuits, such as a tuned differentiator, to detect movement of human tissue compressed within an imaging system using a received movement signal from the movement detection circuit. In some embodiments, the movement analysis module may include hardware and/or software modules configured to accept the movement signal from the movement detection circuit, and detect tissue movement caused by the patient. An exemplary logic flow illustrating movement detection by a movement analysis module is set forth within FIG. 4. By way of example and not limitation, movement may be caused by respiratory activity, cardiac activity, or muscular movements (voluntary or involuntary) by the patient. A movement analysis module may be configured with a movement threshold value, beyond which, movement of the patient is detected and communicated to an image correction module at 608.

At 608, when movement is beyond a threshold, an image correction module may perform a corrective action, which may include one or more of a variety of actions that improve image quality and reduce patient exposure to radiation. An image correction module may be configured to receive a determination from movement analysis module that movement has been detected. The determination may include data indicating a movement time and movement level in some embodiments, and the determination may be used to determine a corrective action to be taken, some of which are described with respect to FIG. 5, and below with respect to FIGS. 7 and 8. Techniques described herein strive to improve image quality, even in situations where movement is detected, reduce patient radiation exposure when possible, and reduce the time required for patients to undergo imaging procedures. While exemplary corrective actions are described herein, other corrective action may be taken consistent with these goals, in some embodiments.

FIG. 7 illustrated a generated image 700 according to an embodiment. Generated image 700 may be generated by one or more imaging systems described herein, for example, imaging systems 100, 200, and/or 300. In some embodiments, corrective actions may include visual indications within a graphical user interface of a display during or after an imaging procedure, using an indicator of an imaging system, and/or using a graphical indication on a generated image itself. FIG. 7 illustrates an alert 702, which may be displayed on a display of an imaging system, indicating to a practitioner or patient that movement was detected during the imaging procedure. Such an indication may alert those viewing the image that quality issues may be fixed by reducing motion in subsequent imaging procedures.

FIG. 8A illustrates a generated image 800 according to an embodiment. Generated image 700 may be generated by one or more imaging systems described herein, for example, imaging systems 100, 200, and/or 300. In some embodiments, corrective actions may include visual indications within a graphical user interface of a display during or after an imaging procedure, using an indicator of an imaging system, and/or using a graphical indication on a generated image itself. FIG. 8A illustrates an alert 802 indicating a motion score, which may indicate a score on a relative scale of motion detected during an imaging procedure. In an example, a minimum and maximum level of movement may be stored within a non-transitory computer-readable storage medium of an imaging system. Once movement has been detected, an image correction module may perform a calculation of the detected movement and determine a score based upon the stored minimum and maximum values, in this manner, a practitioner or patient may be provided with an indication of how much movement was detected, and may take steps to improve image quality in subsequent imaging procedures. In another example, the score may be pass/fail score, with pass meaning that the motion is below the threshold and no corrective action is needed, and fail meaning that corrective action is needed. Other scoring methodologies are contemplated. In one embodiment, the positioning information from many images can be aggregated into analytics and supplied to the facility and other entities for the purposes of training, education, analytics and compliance.

Figure 8B:
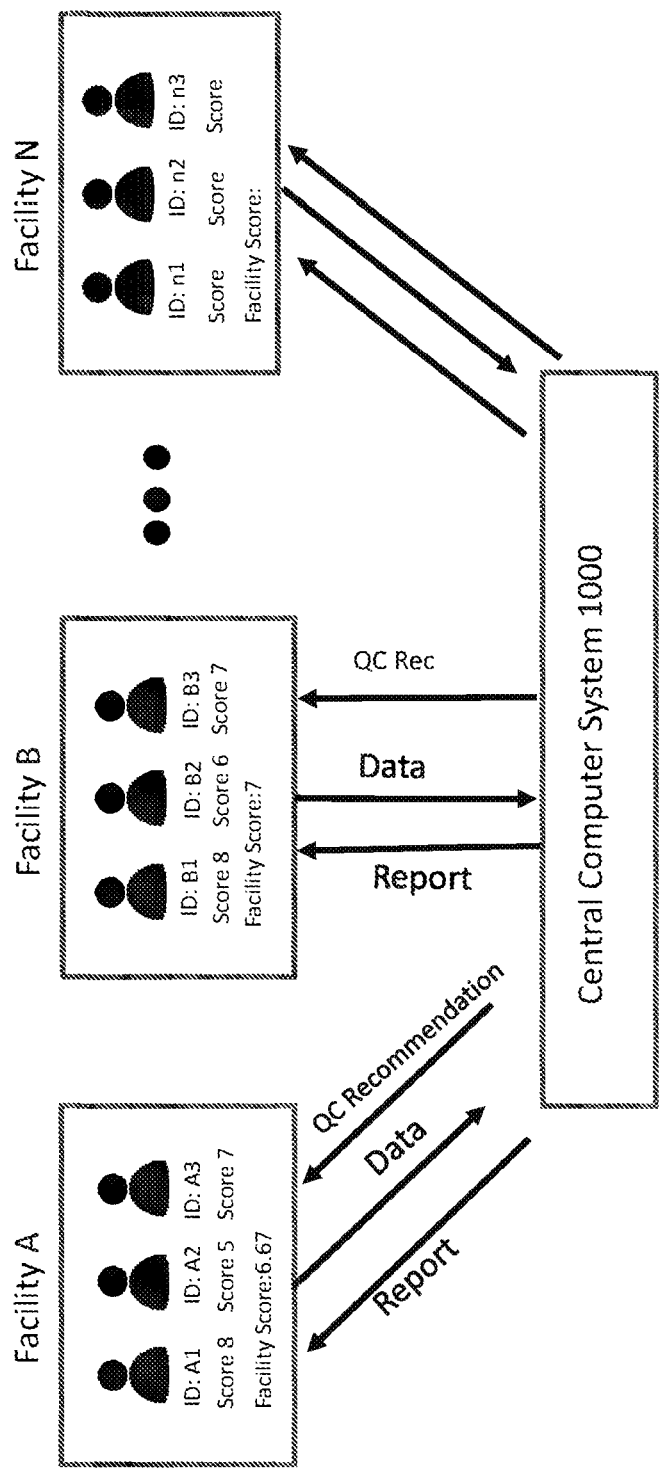
FIG. 8B illustrates a system of facilities according to an embodiment.

FIG. 8B shows the positioning information collected and analyzed according to one embodiment. Each image may be associated with a radiology technologist or technologist who took the image (e.g. a technologist identification number) and associated with a patient positioning score for that image as described above. The information may be stored in the imaging system 100. The information may then be transmitted to a centralized computer system 1000, such as the system 1000 described below with reference to FIG. 10. The centralized computer system 1000 may part of a cloud-computing system. The scores, the technologist IDs, and other information collected from the imaging system 100 may be aggregated over time. The scores for a particular technologist or a particular facility may be analyzed, for example, by the centralized system 1000, to determine if one or more corrective actions are needed. In one example, a particular technologist's average score is compared to average scores of others or other technologists in that particular facility, or in other facilities. In another example, a particular facility's average score may be compared to the average score of other facilities. If the centralized system determined that the technologist's or facility's scores are below a particular threshold, the technologist or members of the facility may be recommended for patient positioning education or quality control improvements. In one example, a look-up table or algorithm determines whether corrective action is needed and what type of action to recommend based in part on the score.

Additional examples of use of the positioning information may include compliance with Federal Regulations, such as the Mammography Quality Standards Act (MQSA) and the Enhancing Quality Using the Inspection Program or EQUIP initiative. The MQSA requires that the images taken at a facility must comply with certain quality standards. Poor positioning is a factor in most deficiencies and failures of clinical images to meet quality standards. EQUIP requires regular review of images, corrective procedures when clinical images are of poor quality, including a mechanism for providing ongoing feedback to technologists or other designated personnel, and oversight of quality control records. The analytics described above can be used to generate reports of compliance with federal regulations. For example, the report may be automatically generated on a periodic basis that includes information such as the score information for that facility, the number of times corrective procedures were taken, the number of times that corrective measures such as education and quality control measures were recommended and were taken. Such reports can be stored and provided if needed to federal regulators to ensure compliance. Complying with EQUIP, however, requires only annual self-reporting from facilities, which has generally resulted in only a yearly review of imaging quality by facilities. Such a lag in reporting may cause downward trends to go unnoticed and potentially poor imaging procedures to occur. In addition, the metrics may be stored in various formats across a plurality of devices and imaging systems, making it even more difficult for the metrics to be monitored. The present technology resolves these problems among others by being able to continuously aggregate quality metrics across a plurality of facilities and provide access and additional insights to those quality metrics in substantially real time as the quality metrics are aggregated. The quality metrics may also be provided to the central computing system in a standardized format via the web application to help ensure that the same types of metrics are properly aggregated and correlated together. Further, due in part to the real time tracking of metrics, warnings and trainings may be provided based on downward trends in image quality before poor imaging procedures may be implemented by technicians of a facility. Such warnings and trainings may provide for an overall improved imaging process for facilities and lead to better detection of abnormalities such as cancers.

FIG. 8C illustrates a logic flow 814 according to an embodiment. The logic flow 814 may be representative of some or all of the operations executed by one or more embodiments described herein, such as systems 100, 200, 300, and/or 1000, for example. In step 804 information, including one or more scores, is received from one or more technologists at a first facility. Positioning information, including one or more scores, is received from one or more technologists at a second facility. In step 806, the information may be analyzed and a report is generated. The report may be provided to the facility for which is it associated. In step 810, the information may be compared. In one example, the scores may be compared within the facility, for instance, to score the technologists relative to each other. In another example, the scores may be compared to scores at other facilities. In step 812, the scores may be compared to a threshold to determine if the particular technologist is above or below the threshold. If above, the technologist is adequately performing positioning patient positioning. If below the threshold, the technologist may require corrective action, for example, education or quality control (QC) corrective actions. In addition, the scores for all the technologists in a particular facility may be compared to a threshold. If the scores for the facility are above the threshold, a report is generated of compliance to federal regulations. If the scores for the facility are below the threshold, QC for the facility are recommended. The thresholds may be those types of predetermined threshold discussed herein. A report is generated with non-compliance and recommendations for QC.

Figure 8D:
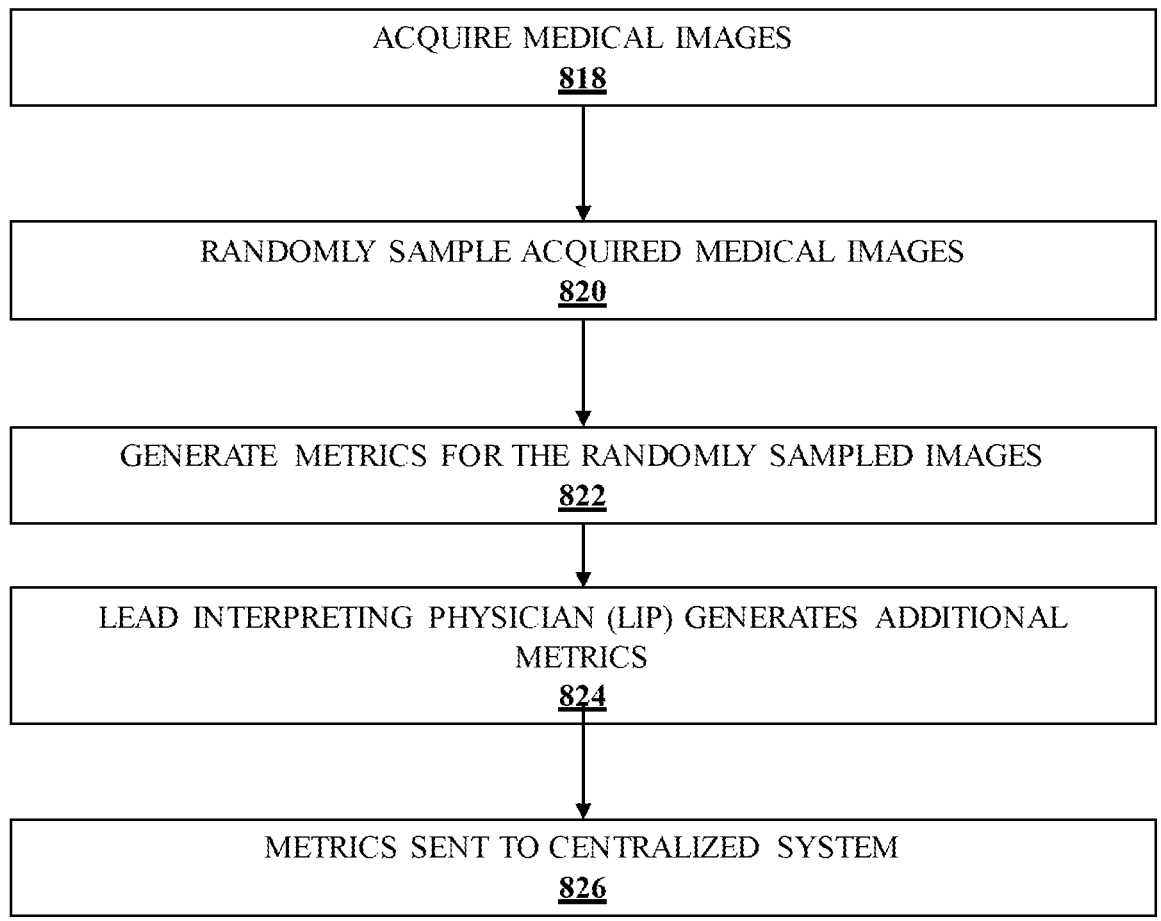
FIG. 8D illustrates a logic flow according to an embodiment.

FIG. 8D illustrates a logic flow or method 816 for processing medical images at a medical facility. The method 816 may be performed by a facility, such as Facility A or B depicted in FIG. 8B. At operation 818, medical images of a patient are acquired. For example, the medical images may be acquired by one or more imaging systems 100 located at the particular facility. The medical images that are acquired may include additional identification information stored with the image, such the identity of the technician that performed the imaging procedure and the identity of the facility that performed the procedure. Such additional identification information may be stored as metadata for the respective medical image, in the header of the medical image, or otherwise stored with the respective medical image such that the additional information is associated with the respective medical image. The identification information may include the name of the patient, an additional patient identifier, the date of examination, the view and laterality of the image, the facility name or identifier and location (e.g., city, state, and zip code of the facility), a technologist identification, a cassette/screen identification, and a mammography unit identification (if there is more than one unit in the facility).

At operation 820, a random sampling of the acquired medical images is taken. The random sampling of images helps reduce potential bias in facilities or technicians selecting images that they believe to be of better quality to artificially inflate their scores or metrics. The random sampling of images may be of images may be for all medical images acquired or of medical images that were actually reviewed by radiologists or other medical professionals. The random sampling may be performed automatically through an interface or software provided by the central computing system to the facility, such as through a web application provided by the central computing system. Random sampling can also be done in real-time (through an algorithm) picking every 3 or 4 or 5 patients, based on the prior volumes/seasonality calculations.

At operation 822, quality metrics are then generated from and/or for the randomly sampled images. The metrics may be automatically generated through patient positioning and/or motion detection algorithms, such as the ones discussed herein and in International Publication No. WO2018/170265, titled "Techniques For Patient Positioning Quality Assurance Prior to Mammographic Image Acquisition," which is incorporated by reference herein in its entirety. The metrics may also be generated by an interpreting physician (IP). For instance, the interpreting physician may review the medical images that have been randomly selected and provide metrics for those medical images. The metrics from the IP may be input into a web application, interface, or other software provided by the central computing system. The metrics that are provided may include positioning metrics, compression metrics, exposure level metrics, contrast metrics, sharpness metrics, noise metrics, and/or artifact metrics, among other metrics. Each metric may also include additional sub-metrics or scores. For example, the positioning metrics may also include sub-metrics such as nipple location, nipple angle, pectoral muscle coverage, inframammary fold visibility, pectoral-nipple line distance, and symmetry between image views. The positioning metrics generally relate to whether sufficient breast tissue is imaged to ensure that cancers or anomalies are not likely to be missed because of inadequate positioning. The compression metrics generally relate to whether compression has been applied in a manner that minimizes the potential obscuring effect of overlying breast tissue and motion artifacts. The exposure level metrics generally relate to whether the exposure level was adequate to visualize breast structures and whether the images were underexposed or overexposed. The contrast metrics generally relate to where the image contrast permitted differentiation of subtle tissue density differences. The sharpness metrics generally relate to whether the margins of normal breast structures were distinct and not blurred. The noise metrics generally relate to whether noise in the image obscured breast structures or suggested the appearance of structures not actually present. The artifacts metrics generally relate to whether artifacts due to lint, processing, scratches, and other factors external to the breast obscured breast structures or suggest the appearance of structures not actually present. The quality metrics may further include metrics or scores based on motion or movement that occurred during imaging the patient. Such motion or movement metrics may be generated using the sensors and techniques discussed herein. The metrics generated at operation 822 may be stored with the medical image(s) for which the metrics were generated.

At operation 824 a lead interpreting physician (LIP) may generate additional metrics for the medical images for which the metrics were generated in operation 822. The LIP may generate metrics for all of those images or a subset of those images. The subset of the images may be a randomized subset of images. The LIP may in some cases modify or confirm the metrics generated in operation 822. In other examples, the LIP may generate additional metrics for the medical images. Any metrics generated by the LIP may also be stored with the medical images. At operation 826, the metrics for medical images are sent from the facility to the central computing system. The medical images may also be sent with the metrics in some examples. In other examples the metrics and at least a portion of the identification information may be sent as correlated to one another, such as in the same report or otherwise linked in an exported database.

Figure 8F:
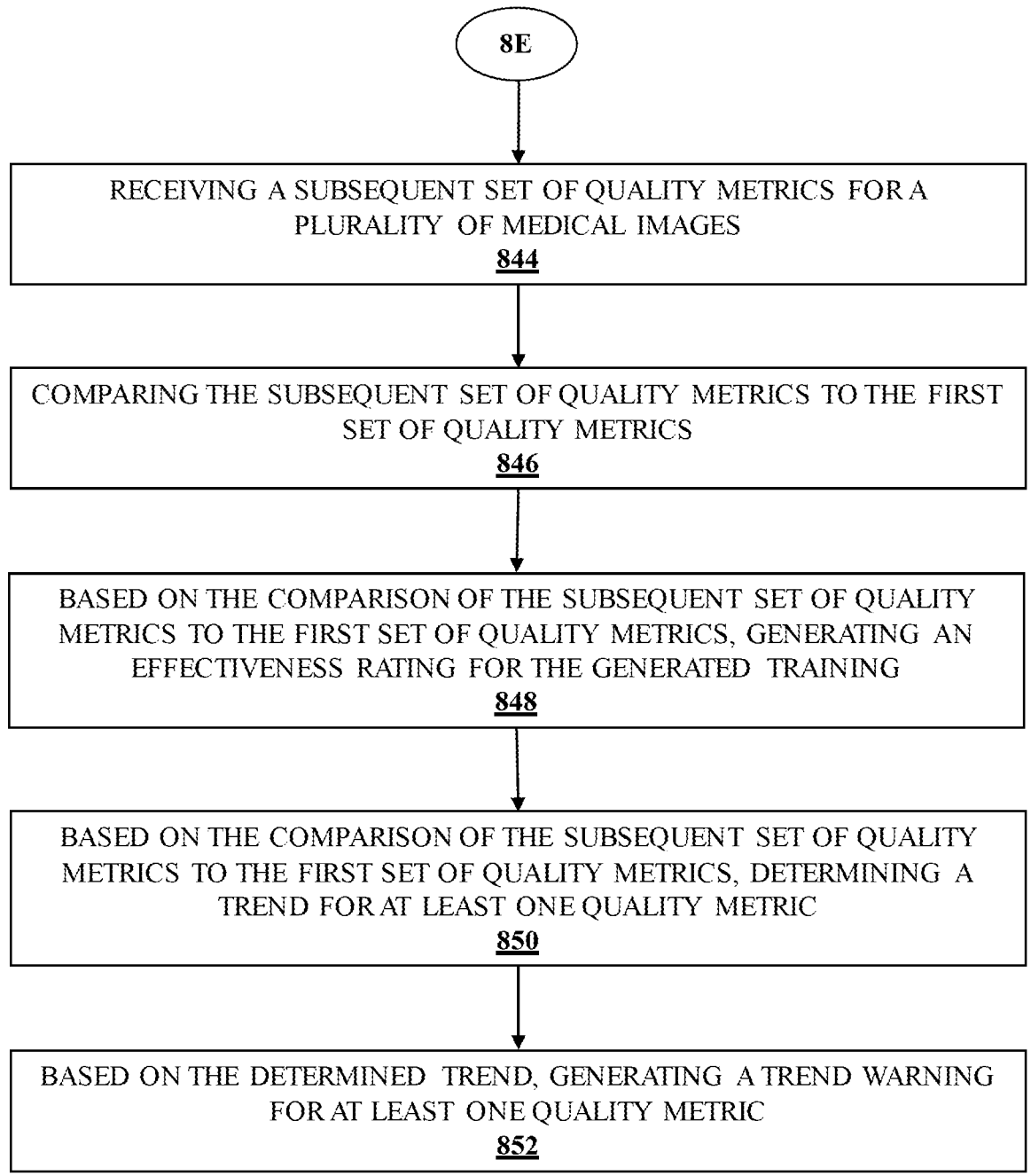
FIG. 8F illustrates a logic flow according to an embodiment.

FIGS. 8E and 8F depict a logic flow or method 828 for processing medical image metrics at a central computing system. For example, the method 828 may be performed by the central computing system to aggregate and process quality metrics from a plurality of facilities. At operation 830, a first set of quality metrics for a plurality of medical images are received from a first imaging facility, such as Facility A in FIG. 8B. The quality metrics received may also include the identification information for the medical images for which the received quality metrics correspond. In some examples, the medical images themselves may also be received. At operation 832, a second set of quality metrics for a plurality of medical images are received from a second imaging facility, such as Facility B in FIG. 8B. The quality metrics received may also include the identification information for the medical images for which the received quality metrics correspond. In some examples, the medical images themselves may also be received. While not shown in FIG. 8E, method 828 may also include receiving additional quality metrics from additional facilities. In addition, the quality metrics received from the first facility and the second facility may be ongoing. For example, the first facility and the second facility may send quality metrics at regular intervals, such as monthly or quarterly. When the quality metrics are received by the central computing system, the central computing system may continue to store the metrics to track trends from different facilities. In some examples, the metrics are received through a web application provided to the facilities by the central computing system. For instance, the IP and LIP may directly enter the metrics into the web application, which causes the receipt of the metrics by the central computing system. The identification information may also be provided in the web application and/or the web application or the central computing system may extract the identification information from the medical images At operation 834, the first set of quality metrics are compared to the second set of quality metrics. For example, once the first and second sets of quality metrics are received, the central computing system may cause the two sets of metrics to be compared to one another. In other examples where additional metrics are received from additional facilities, those metrics may also be compared to one another. In some examples, individual metrics from the first set may be compared to the corresponding individual metric of the other set. For instance, positioning metrics for the first facility may be compared to positioning metrics of the second facility. At operation 836, based on the comparison of the first set of quality metrics to the second set of quality metrics, a benchmark is set for at least one metric in the first set of quality metrics and the second set of quality metrics. The benchmark may be standard or point of reference against which the quality metrics may be assessed. For example, based on the comparison of the aggregated quality metrics from the plurality of facilities, the average patient positioning score may be determined. That average patient positioning score may then be used as a benchmark for an individual facility to determine how it is performing as compared to that benchmark. Benchmarks other than average scores may also be determined including benchmarks based on different statistical analyses such as percentiles. Benchmarks may also be set by government entities, such as the FDA. The benchmarks may also be based on the type of facility. For example, benchmarks may be created for facilities that are similarly situated based on factors such as location, number of technicians, number of medical images acquired, number of imaging systems on site, number of interpreting physicians, or other characteristics of the facilities. Accordingly, facilities may be able to compare their own quality metrics against benchmarks that are derived from the like facilities.

At operation 838, a dashboard may be provided by the central computing system one or more of the facilities from which quality metrics are received. The dashboard may be provided to the facility through the web application. Facility data for a facility or a particular technologist may be generated based on the generated benchmark in operation 836 and the first set of quality metrics and/or the second set of quality metrics. The facility data may include the quality metrics from one or more facilities compared to the benchmark(s) generated in operation 836. The facility data may be presented in the dashboard. For instance, the facility data and/or quality metrics for the facility accessing the dashboard may be viewed through the dashboard. For example, an LIP or other member of the facility may access the dashboard to see how the facility's quality metrics compare to the benchmark quality metrics and/or the quality metrics of other facilities. The quality metrics may be searched or refined as well through the dashboard. The LIP may refine the quality metrics based on a period of time or for a certain technician or technicians. For instance, if the LIP wanted to see how a particular technician performed over a certain month, the LIP could refine the results in the dashboard to see such information. Reports regarding the quality metrics of the facility may also be generated through the dashboard. The dashboard may also be used to track how the facility's quality metrics compare to federal regulations and provide warnings if the metrics are below federal regulations for any time period. Reports may also be generated that indicate how the quality metrics of the facility compare to federal regulations or guidelines. In addition, a dashboard may also be provided to a government agency or review board to show how an individual facility is performing or to show how a group of facilities is performing. The dashboard also provides useful insights into the quality metrics that were previously unavailable. As the metrics are received by the central computing system, the dashboard representation for the facility may be updated almost immediately. Accordingly, the imaging quality of a facility is able to be tracked over time and in a real time or live manner that has never been available before.

The dashboard or the reports may also provide additional insights beyond the metrics that are reported. For instance, based on the aggregation of the quality metrics, a large enough sample of metrics across different facilities may allow for correlations between different types of quality metrics and the identifying data. Such correlations and insights may be generated through machine learning techniques. Unsupervised machine learning techniques may be particularly useful in identifying correlations and insights that may have been previously unknown. Clustering-based, association-based, and anomaly-based unsupervised learning algorithms, among others, may all be used for the data. Clustering algorithms are generally directed to problems where the goal is to discover inherent clusters or grouping of data, and association algorithms are generally directed to problems where the goal is to discover rules that describe large portions of data. Anomaly detection algorithms generally are directed to discovering unusual or outlier metrics within the set of quality metrics. As an example, the aggregated metrics and identification data may be provided as an input to the unsupervised machine learning algorithms to output previously unknown structures, patterns, and associations within the aggregated metrics and identification data.

At operation 840, a training recommendation for a facility or a particular technologist may be generated based on the generated benchmark in operation 836. The training recommendation may be generated by the central computing system. For example, based on a comparison of the first set of quality metrics to the generated benchmark, it may be determined that the first set of quality metrics (or a subset thereof) are falling short of the benchmark. Based on that determination, a training recommendation may be provided. As an example, the positioning metrics for a particular technician may be below a benchmark or a federal regulation or guideline. A training for that technician regarding positioning may then be generated by operation 840. The training may also be tailored to the specific positioning metrics that are problematic for the specific technician. The trainings may be generated from training sets available from different training organizations or custom trainings provided by the company hosting or operating the central computing system. For instance, the trainings may be a set of videos for the technician to watch to better understand how to properly position the patient. The video trainings may also include interactive elements that further improve the interaction of the technician during the training. Such interactive trainings may also include an assessment following or during the training that assesses how well the technician is understanding the information provided by the training. The generated training may also include recommendations for programs that are available based on the particular problematic metrics.

At operation 842, the training generated in operation 840 is sent to the facility. For example, when the training has been generated for a technician at the first facility, the generated training is sent to the first facility. The training may be sent to the first facility by the central computing system via the web application or other form of communication. The training may be in the form as a series of videos that are accessible via the web application by the technician. Similarly, interactive trainings may also be provided via the web application. During the interactive trainings, an assessment score may be stored that indicates how well the technician performed during the training. That assessment score may be stored and associated with that technician for the particular training that was generated at operation 840.

At operation 844 (shown in FIG. 8F), a subsequent set of quality metrics for a plurality of medical images is received. For example, the central computing system may receive, from the first imaging facility, a subsequent set of quality metrics for a plurality of medical images that were acquired after the medical images for which metrics were receiving in operation 830. Subsequent sets of quality metrics may also be received from additional facilities as well. As discussed above, the quality metrics may be continuously received from the facilities as the quality metrics are generated. In some examples, the subsequent set of quality metrics may be received from a facility that has received and/or completed the training sent in operation 842.

At operation 846, the subsequent set of quality metrics are compared to quality metrics previously received by one or more of the imaging facilities. For example, when the subsequent quality metrics are received from the first imaging facility, those subsequent quality metrics are compared to the first set of quality metrics received in operation 830. At operation 848, based on the comparison of the subsequent quality metrics to the prior quality metrics, such as the first set of quality metrics, an effectiveness rating for a training is generated. The effectiveness rating may be generated for the training that was generated in operation 840 and sent to the facility in operation 842. The effectiveness rating indicates how effective the training was that was provided to the facility and/or the technician.

As an example, the training is provided to the first facility after the first set of quality metrics are received and the subsequent set of quality metrics are received after the training has been completed. Due to the training being completed, the expectation is that the quality metrics for the facility will have improved. A comparison between the subsequent set of quality metrics and the first set of quality metrics can either confirm or refute that expectation. For instance, if the training was for patient positioning, the patient positioning metrics from the first set of quality metrics are compared to the patient positioning metrics from the subsequent set of quality metrics. If the subsequent positioning metric improved, a positive effectiveness rating is generated for the training to indicate that the training is effective. If the subsequent positioning metric remained the same, a neutral effectiveness rating is generated for the training to indicate that the training is ineffective. If the subsequent positioning metric worsened, a negative effectiveness rating is generated for the training to indicate that the training is counterproductive. The effectiveness rating may then be used as feedback to the central computing system in generating future trainings. For example, trainings that have received a negative effectiveness rating may no longer be generated and sent to facilities, whereas trainings that have received a positive effectiveness rating may be more heavily weighted in generating future trainings.

In some examples, generating the effectiveness rating of the training may account for the assessment scores of the technicians that received the training. As discussed above, during the interactive trainings, an assessment score may be stored that indicates how well the technician performed during the training. If the assessment score is low for the training and the subsequent quality metric did not improve, the training itself may not be ineffective. Rather, the low-scoring technician may need additional more in-depth training and assistance. In such examples where the assessment score is low, a lower weight may be assigned to the effectiveness rating of the training.

At operation 850, a trend is determined for at least one quality metric based on the comparison of the subsequent set of metrics and the prior set of quality metrics performed in operation 846. In some examples, the determination of the trend may be performed as part of operation 848. For instance, as discussed above, particular metrics may be compared to one another to determine whether the metric has improved or worsened over time. That trend and the rate of the trend is determined in operation 850. The rate of the trend may be based on the total change in the particular metric over a designated period of time, such as days, weeks, months, quarters, or years.

At operation 852, a warning or notification may be generated based on the trend determined in operation 850. The generation of the warning may be based on the rate of the trend as well. For instance, if the trend is negative and the rate of the trend is above a predetermined threshold, a warning may be generated and send to the facility that has the rapidly worsening metric. Such a warning may prevent poor imaging procedures before they occur because the facility can implement corrections upon receiving the warning. The warning may also be based on a negative trend and a metric that is approaching a benchmark and/or federal guideline or regulation. For example, where a quality metric is within a predetermined threshold of a benchmark and/or federal guideline or regulation and the trend is negative, a warning may be generated and provided to the facility. By providing such a warning, the facility is able to implement corrections before falling below the benchmark or being out of compliance with the issued guideline or regulation.

Figure 9:
FIG. 9 illustrates an article of manufacture according to an embodiment.

FIG. 9 illustrates an article of manufacture according to an embodiment. Storage medium 900 may comprise any computer-readable storage medium or machine-readable storage medium, such as an optical, magnetic or semiconductor storage medium. In some embodiments, storage medium 900 may comprise a non-transitory storage medium. In various embodiments, storage medium 900 may comprise an article of manufacture. In some embodiments, storage medium 900 may store computer-executable instructions, such as computer-executable instructions to implement logic flow 900, for example. Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The embodiments are not limited to these examples.

Figure 10:
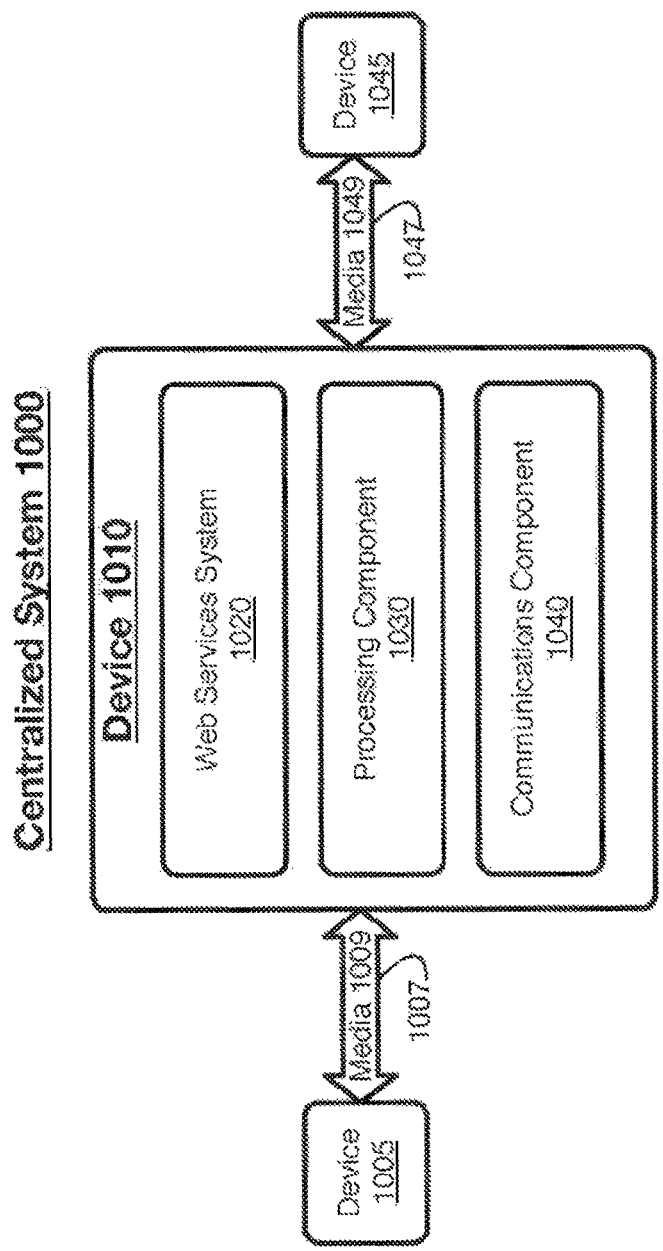
FIG. 10 illustrates an embodiment of a centralized system.

FIG. 10 illustrates a block diagram of a centralized system 1000. The centralized system 1000 may implement some or all of the structure and/or operations for the web services system 1020 in a single computing entity, such as entirely within a single device 1010.

The device 1010 may comprise any electronic device capable of receiving, processing, and sending information for the web services system 1020. Examples of an electronic device may include without limitation an imaging system, client device, a mobile computing device, a computer, a server, a distributed computing system, multiprocessor systems, or combination thereof. The embodiments are not limited in this context.

The device 1010 may execute processing operations or logic for the web services system 1020 using a processing component 1030. The processing component 1030 may comprise various hardware elements, software elements, or a combination of both. Examples of hardware elements may include devices, logic devices, microprocessors, circuits, circuit elements (e.g., transistors, resistors, capacitors, inductors, and so forth), integrated circuits, and so forth. Examples of software elements may include software programs, machine programs, operating system software, middleware, firmware, functions, methods, procedures, software interfaces, application program interfaces (API), words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The device 1010 may execute communications operations or logic for the web services system 1020 using communications component 1040. The communications component 1040 may implement any well-known communications techniques and protocols, such as techniques suitable for use with packet-switched networks (e.g., public networks such as the Internet, private networks such as an enterprise intranet, and so forth), circuit-switched networks (e.g., the public switched telephone network), or a combination of packet-switched networks and circuit-switched networks (with suitable gateways and translators). The communications component 1040 may include various types of standard communication elements, such as one or more communications interfaces, network interfaces, wireless transmitters/receivers (transceivers), wired and/or wireless communication media, physical connectors, and so forth. By way of example, and not limitation, communication media 1009, 1049 include wired communications media and wireless communications media, The device 1010 may communicate with other devices 1005, 1045 over a communications media 1009, 1049, respectively, using communications signals 1007, 1047, respectively, via the communications component 1040. The devices 1005, 1045, may be internal or external to the device 1010 as desired for a given implementation.

For example, device 1005 may correspond to a client device such as a phone used by a user. Signals 1007 sent over media 1009 may therefore comprise communication between the phone and the web services system 1020 in winch the phone transmits a request and receives a web page or other data, in response.

Figure 11:
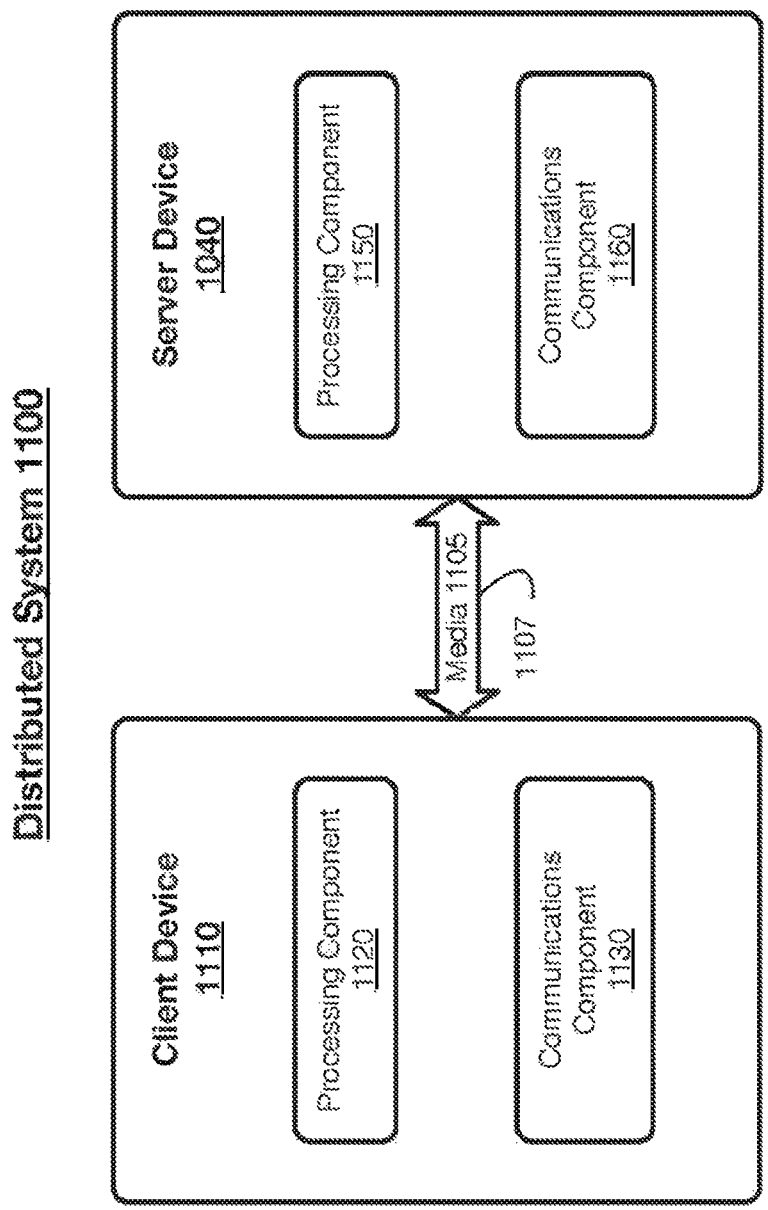
FIG. 11 illustrates an embodiment of a distributed system.

FIG. 11 illustrates a block diagram of a distributed system 1100. The distributed system 1100 may distribute portions of the structure and/or operations for the disclosed embodiments across multiple computing entities. Examples of distributed system 00 may include without limitation a client-server architecture, a peer-to-peer architecture, a shared database architecture, and other types of distributed systems. The embodiments are not limited in this context.

The distributed system 1100 may comprise a client device 1110 and a server device 1140. In general, the client device 1110 and the server device 1140 may be the same or similar to the client device 1010 as described with reference to FIG. 10. For instance, the client system 1110 and the server system 1140 may each comprise a processing component 1120, 1150 and a communications component 1130, 1160 which are the same or similar to the processing component 1030 and the communications component 1040, respectively, as described with reference to FIG. 10. In another example, the devices 1110, 1140 may communicate over a communications media 1105 using communications signals 1107 via the communications components 1130, 1160.

The client device 1110 may comprise or employ one or more client programs that operate to perform various methodologies in accordance with the described embodiments. In one embodiment, for example, the client device 1110 may implement some steps described with respect to FIGS. 4-6.

The server device 1140 may comprise or employ one or more server programs that operate to perform various methodologies in accordance with the described embodiments. In one embodiment, for example, the server device 40 may implement some steps described with respect to FIGS. 4-6.

Figure 12:
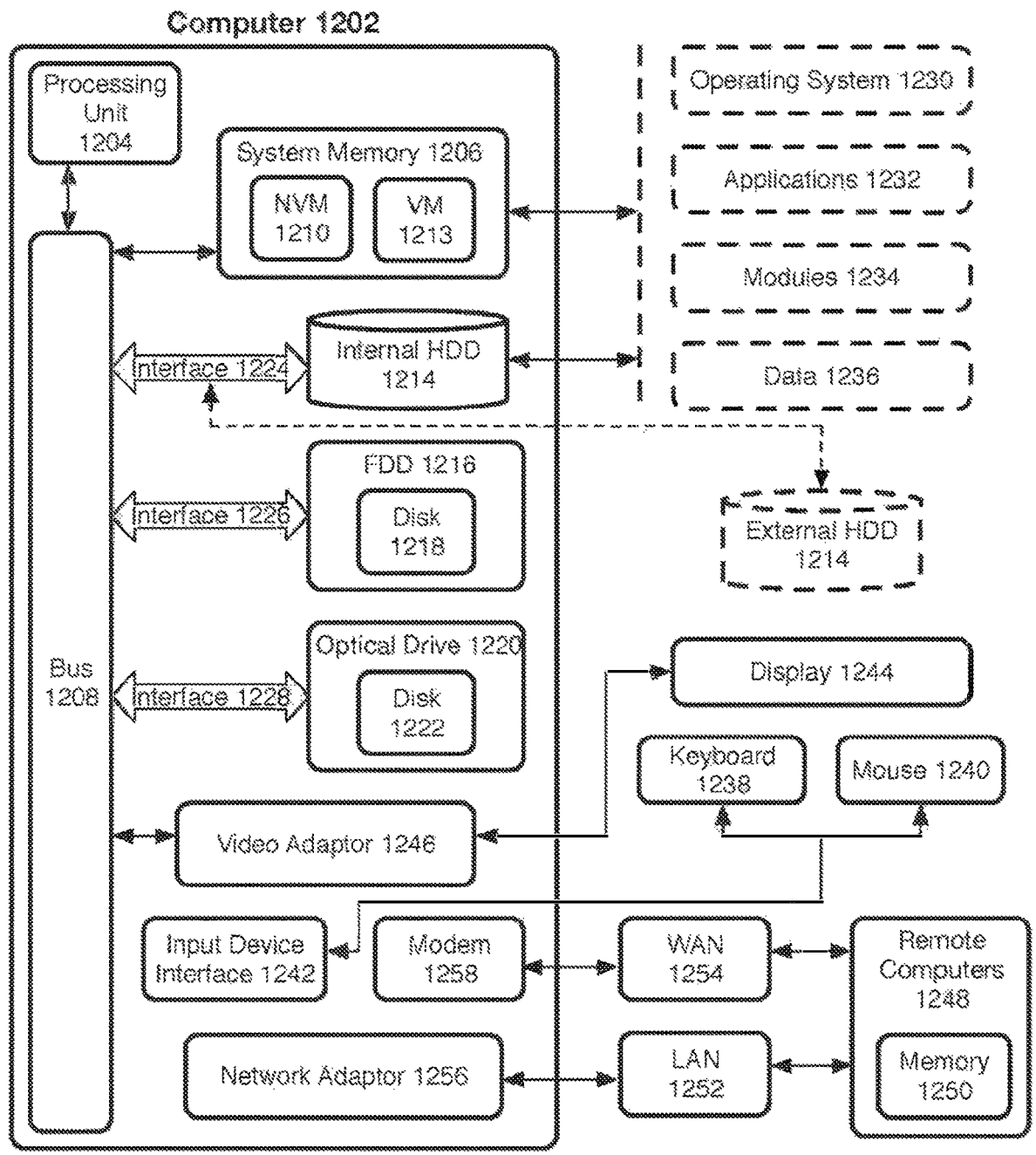
FIG. 12 illustrates an embodiment of a computing architecture.

FIG. 12 illustrates an embodiment of an exemplary computing architecture 1200 suitable for implementing various embodiments as previously described. In one embodiment, the computing architecture 1200 may comprise or be implemented as part of an electronic device. Examples of an electronic device may include those described herein. The embodiments are not limited in this context.

As used in this application, the terms "system" and "component" are intended to refer to a computer-related entity, either hardware, a combination of hardware and software, software, or software in execution, examples of which are provided by the exemplary computing architecture 1200. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the unidirectional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1200 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1500.

As shown in FIG. 12, the computing architecture 1200 comprises a processing unit 1204, a system memory 1206 and a system bus 1208. Dual microprocessors, multi-core processors, and other multi-processor architectures may also be employed as the processing unit 1204.

The system bus 1208 provides an interface for system components including, but not limited to, the system memory 1206 to the processing unit 1204. The system bus 1208 can be any of several types of bus structure that may further interconnect to a memory bus (with or without a memory controller), a peripheral bus, and a local bus using any of a variety of commercially available bus architectures. Interface adapters may connect to the system bus 1208 via a slot architecture, for example.

The computing architecture 1200 may comprise or implement various articles of manufacture. An article of manufacture may comprise a computer-readable storage medium to store logic, as described above with respect to FIG. 9.

The system memory 1206 may include various types of computer-readable storage media in the form of one or more higher speed memory units, such as read-only memory (ROM), random-access memory (RAM), dynamic RAM (DRAM), solid state memory devices (e.g., USB memory, solid state drives (SSD) and any other type of storage media suitable for storing information). In the illustrated embodiment shown in FIG. 12, the system memory 1206 can include non-volatile memory 1210 and/or volatile memory 1213. A basic input/output system (BIOS) can be stored in the non-volatile memory 1210.

The computer 1202 may include various types of computer-readable storage media in the form of one or more lower speed memory units, including an internal (or external) hard disk drive (HDD) 1214, a magnetic floppy disk drive (FDD) 1216 to read from or write to a removable magnetic disk 1218, and an optical disk drive 1220 to read from or write to a removable optical disk 1222 (e.g., a CD-ROM, DVD, or Blu-ray). The HDD 1214, FDD 1216 and optical disk drive 1220 can be connected to the system bus 1208 by a HDD interface 1224, an FDD interface 1226 and an optical drive interface 1228, respectively. The HDD interface 1224 for external drive implementations can include at least one or both of Universal Serial Bus (USB) and IEEE 1394 interface technologies.

The drives and associated computer-readable media provide volatile and/or nonvolatile storage of data, data, structures, computer-executable instructions, and so forth. For example, a number of program modules can be stored in the drives and memory units 1210, 1213, including an operating system 1230, one or more application programs 1232, other program modules 1234, and program data 1236. In one embodiment, the one or more application programs 1232, other program modules 1234, and program data 1236 can include, for example, the various applications and/or components to implement the disclosed embodiments.

A user can enter commands and information into the computer 1202 through one or more wire/wireless input devices, for example, a keyboard 1238 and a pointing device, such as a mouse 1240. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1204 through an input device interface 1242 that is coupled to the system bus 1208, but can be connected by other interfaces such as a parallel port, IEEE 1394 serial port, a game port, a USB port, an IR interface, and so forth.

A display 1244 is also connected to the system bus 1208 via an interface, such as a video adaptor 1246. The display 1244 may be internal or external to the computer 1202. In addition to the display 1244, a computer typically includes other peripheral output devices, such as speakers, printers, and so forth.

The computer 1202 may operate in a networked environment using logical connections via wire and/or wireless communications to one or more remote computers, such as a remote computer 248. The remote computer 1248 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1250 is illustrated. The logical connections depicted include wire/wireless connectivity to a local area network (LAN) 1252 and/or larger networks, for example, a wide area network (WAN) 1254. Such LAN and WAN networking environments are commonplace in offices and companies, and facilitate enterprise-wide computer networks, such as intranets, all of which may connect to a global communications network, for example, the Internet.

When used in a LAN networking environment, the computer 1202 is connected to the LAN 1252 through a wire and/or wireless communication network interface or adaptor 1256. The adaptor 1256 can facilitate wire and/or wireless communications to the LAN 1252, which may also include a wireless access point disposed thereon for communicating with the wireless functionality of the adaptor 1256.

When used in a WAN networking environment, the computer 1202 can include a modem 1258, or is connected to a communications server on the WAN 1254, or has other means for establishing communications over the WAN 1254, such as by way of the Internet. The modem 1258, which can be internal or external and a wire and/or wireless device, connects to the system bus 1208 via the input device interface 1242. In a networked environment, program modules depicted relative to the computer 1202, or portions thereof, can be stored in the remote memory/storage device 1250. It will be appreciated that the network connections shown are exemplary and other means of establishing a communications link between the computers can be used.

The computer 1202 is operable to communicate with wire and wireless devices or entities using the IEEE 802 family of standards, such as wireless devices operatively disposed in wireless communication (e.g., IEEE 802.1 1 over-the-air modulation techniques). This includes at least Wi-Fi (or Wireless Fidelity), WiMax, and Bluetooth™ wireless technologies, among others.

Figure 13:
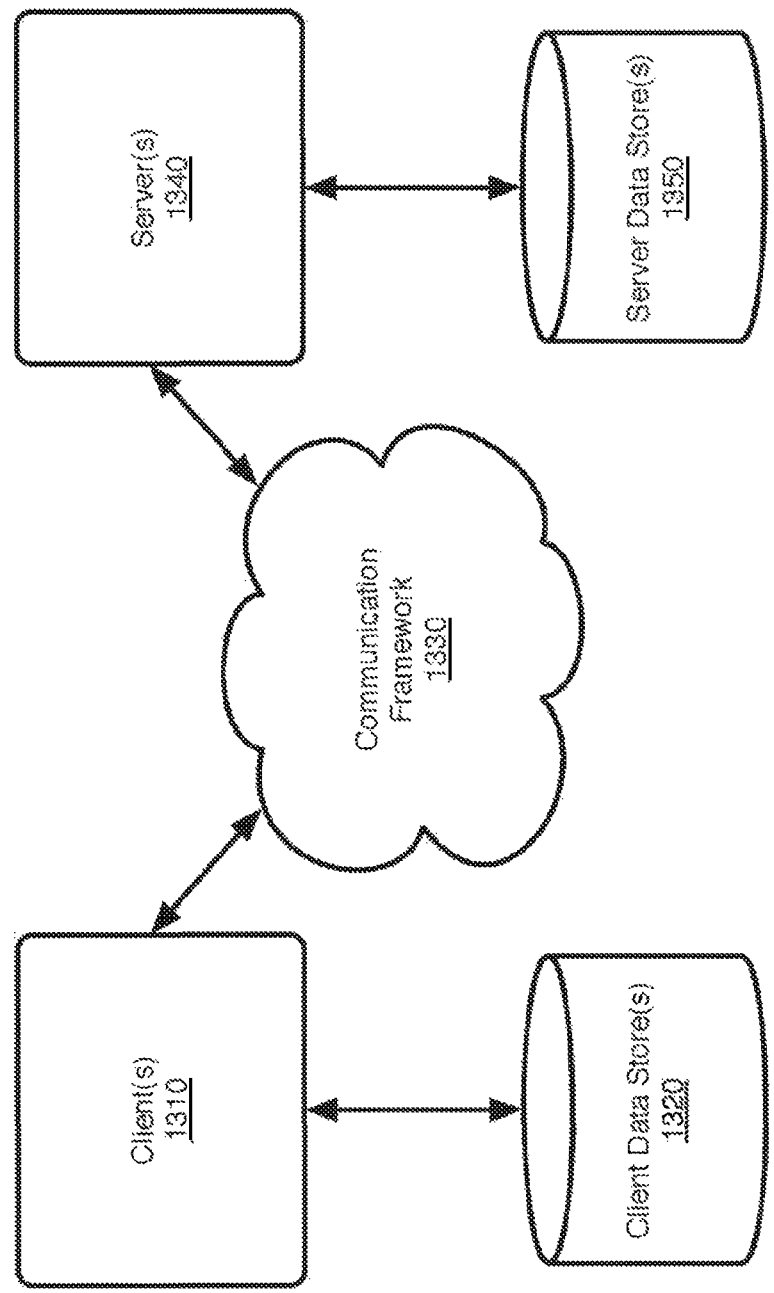
FIG. 13 illustrates an embodiment of a communications architecture.

FIG. 13 illustrates a block diagram of an exemplary communications architecture 300 suitable for implementing various embodiments as previously described. The communications architecture 1300 includes various common communications elements, such as a transmitter, receiver, transceiver, radio, network interface, baseband processor, antenna, amplifiers, filters, power supplies, and so forth. The embodiments, however, are not limited to implementation by the communications architecture 1300.

As shown in FIG. 13, the communications architecture 1300 comprises includes one or more clients 1310 and servers 1340. The clients 1310 may implement the client device 1110, for example. The servers 1340 may implement the server device 1140, for example. The clients 1310 and the servers 340 are operatively connected to one or more respective client data stores 1320 and server data stores 1350 that can be employed to store information local to the respective clients 1310 and servers 1340, such as cookies and/or associated contextual information.

The clients 1310 and the servers 1340 may communicate information between each other using a communication framework 1330. The communications framework 1330 may implement any well-known communications techniques and protocols. The communications framework 1330 may be implemented as a packet-switched network (e.g., public networks such as the Internet, private networks such as an enterprise intranet, and so forth), a circuit-switched network (e.g., the public switched telephone network), or a combination of a packet-switched network and a circuit-switched network (with suitable gateways and translators).

The communications framework 1330 may implement various network interfaces arranged to accept communicate, and connect to a communications network. A network interface may be regarded as a specialized form of an input output interface. Network interfaces may employ connection protocols including without limitation direct connect, Ethernet, wireless network interfaces, cellular network interfaces, and the like.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible.

What is claimed is:

1. A method of imaging breast tissue to ensure adequate compression of the breast tissue by a breast imaging system, the method comprising:
   generating, by a plurality of sensors disposed in a pattern throughout at least one of a breast compression paddle or an imaging detector, wherein the imaging detector is disposed a distance away from and parallel to the breast compression paddle and the plurality of sensors include one or more of photo sensors, infrared sensors and ultrasonic sensors, a plurality of signals indicative of the breast tissue compressed between the breast compression paddle and the imaging detector;
   generating, at a first time point, first spatial data of the breast tissue based on the plurality of force signals;
   generating, by the compression contours module integrated within the breast imaging system, based on the first spatial data, a contact map for the compressed breast;
   based on generating the contact map, determining a value for a roll-off region;
   in response to determining the value for the roll-off region, delaying, by a compression adequacy analysis module incorporated into the breast imaging system, image capture of the breast tissue by the breast imaging system as long as the determined value for the roll-off region exceeds a predetermined threshold for the roll-off region; and
   based on the at least one of the contact map or the comparison, generating, at a display incorporated into the breast imaging system, a notification that the breast is in at least one of an improper compression or an improper position.

2. The method of claim 1, further comprising:
   generating, at a second time point, second spatial data of the breast based on data captured by the at least one sensor;
   based on the first spatial data and the second spatial data, determining an amount of motion of the breast that occurred between the first time point and the second time point; and
   based on the determined amount of motion performing at least one of:
      generating a motion map for the breast;
      discarding one or more acquired projections for use in generating a tomosynthesis reconstruction; or
      correcting a medical image acquired at substantially the second time point.

3. The method of claim 2, further comprising:
   comparing the determined amount of motion to a predetermined threshold; and
   wherein discarding one or more acquired projections is based on the comparison.

4. The method of claim 2, wherein the motion map includes magnitudes of motion for a plurality of different regions of the breast.

5. The method of claim 2, further comprising, based on the determined amount of motion, generating a correction map.

6. The method of claim 1, wherein the value for the roll-off region is at least one of: an area of the roll-off region, a maximum distance between an uncompressed breast line and a skin line of the breast, a minimum distance between the uncompressed breast line and the skin line, or a ratio between the area of the roll-off region and an area of the entire breast.

7. The method of claim 1, wherein the at least one sensor includes at least one of an optical sensor, an infrared sensor, or an ultrasonic sensor.

8. The method of claim 1, wherein the at least one sensor includes a set of sensors incorporated into the breast compression paddle and the imaging detector.

9. The method of claim 1, wherein the at least one sensor is an ultrasound sensor, and the first spatial data includes data of internal breast tissue.

10. The method of claim 1, wherein the at least one sensor includes a set of sensors incorporated into the breast compression paddle and the imaging detector.

11. The method of claim 1, wherein the contact map includes a skin line for the breast, an uncompressed breast line, and a roll-off region between the uncompressed breast line and the skin line.

12. The method of claim 1, further comprising generating, based on the first spatial data, positional data.

13. The method of claim 12, wherein the positional data includes data based on the position of a pectoral muscle.

14. The method of claim 13, further comprising determining, based on the positional data, whether the pectoral muscle is properly positioned such that it will be imaged by the imaging system.

15. The method of claim 12, wherein the positional data includes data based on positioning of a nipple.

16. The method of claim 15, further comprising assessing, based on the positional data, alignment of the nipple, by determining a posterior nipple line (PNL).

17. The method of claim 1, wherein the at least one sensor includes a force sensor to generate a force signal indicating a measure of force applied to the breast and the method further comprises:
   filtering, by a movement detection circuit, a movement signal from the force signal indicative of a measure of movement of the breast; and
   determining, by a movement analysis module, that the movement signal is beyond a movement threshold.

18. The method of claim 1, wherein the plurality of sensors are arranged in a grid pattern.

19. The method of claim 1, wherein the plurality of sensors are disposed around a periphery of at least one of the breast compression paddle and the imaging detector.

* * * * *